United States Patent
Lyerly et al.

(10) Patent No.: US 9,956,276 B2
(45) Date of Patent: May 1, 2018

(54) VACCINES AGAINST ANTIGENS INVOLVED IN THERAPY RESISTANCE AND METHODS OF USING SAME

(71) Applicant: Duke University, Durham, NC (US)

(72) Inventors: Herbert K. Lyerly, Durham, NC (US); Michael A. Morse, Durham, NC (US); Takuya Osada, Durham, NC (US); Timothy M. Clay, Waterloo (BE); Zachary C. Hartman, Durham, NC (US)

(73) Assignee: Duke University, Durham, NC (US)

( * ) Notice: Subject to any disclaimer, the term of this patent is extended or adjusted under 35 U.S.C. 154(b) by 2 days.

(21) Appl. No.: 14/373,103

(22) PCT Filed: Jan. 21, 2013

(86) PCT No.: PCT/US2013/022396
§ 371 (c)(1),
(2) Date: Jul. 18, 2014

(87) PCT Pub. No.: WO2013/110030
PCT Pub. Date: Jul. 25, 2013

(65) Prior Publication Data
US 2014/0377261 A1    Dec. 25, 2014

Related U.S. Application Data

(60) Provisional application No. 61/588,449, filed on Jan. 19, 2012.

(51) Int. Cl.
*A61K 39/00* (2006.01)
*C07K 16/32* (2006.01)
*A61K 31/517* (2006.01)
*A61K 45/06* (2006.01)

(52) U.S. Cl.
CPC ........ *A61K 39/0011* (2013.01); *A61K 31/517* (2013.01); *A61K 45/06* (2013.01); *C07K 16/32* (2013.01); *A61K 2039/505* (2013.01); *A61K 2039/507* (2013.01); *A61K 2039/5256* (2013.01); *A61K 2039/53* (2013.01); *C07K 2317/73* (2013.01); *C07K 2317/734* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 2003/0143568 A1* | 7/2003 | Singer | C07K 14/71 435/6.11 |
| 2003/0232350 A1 | 12/2003 | Afar et al. | |
| 2004/0253606 A1 | 12/2004 | Aziz et al. | |
| 2005/0266409 A1 | 12/2005 | Brown et al. | |
| 2008/0057064 A1* | 3/2008 | Zhou | A61K 39/0011 424/139.1 |
| 2009/0214518 A1 | 8/2009 | Buckanovich et al. | |
| 2010/0279399 A1 | 11/2010 | Robins et al. | |
| 2011/0281748 A1 | 11/2011 | Singh et al. | |
| 2012/0014984 A1 | 1/2012 | Shahabi | |
| 2014/0017259 A1* | 1/2014 | Aurisicchio | A61K 38/179 424/172.1 |
| 2014/0221329 A1 | 8/2014 | Yelenski et al. | |

FOREIGN PATENT DOCUMENTS

| | | | | |
|---|---|---|---|---|
| WO | WO 01/38576 A2 * | 5/2001 | | C12Q 1/68 |
| WO | WO 2003/080835 | 10/2003 | | |
| WO | WO 2008/049930 | 5/2008 | | |
| WO | WO 2011/146568 | 11/2011 | | |
| WO | WO 2012/125864 | 9/2012 | | |
| WO | WO 2012/125864 A2 * | 9/2012 | | A61K 39/395 |

OTHER PUBLICATIONS

Holmes (Exp. Opin.Invest. Drugs, 2001, 10(3):511-519).*
Tanaka et al. (1985 Proc. Natl. Acad. Sci USA 82:3400-3404).*
Greenspan et al. (Nature Biotechnology 7:936-937 (1999).*
Ono et al. (Proc. Natl. Acad. Sci. USA 86: 4868-4871).*
Castiglioni et al. Role of exon-16-deleted HER2 in breast carcinomas. (2006) Endocr Relat Cancer: 13(1): 221-232.
GenBank NM_000125.3. *Homo sapiens* estrogen receptor 1 (ESR1), transcript variant 1, mRNA [online] Oct. 2, 2011 [retrieved Sep. 10, 2015]. Available on the internet: <URL: http://www.ncbi.nlm.nih.gov/nuccore/170295798?sat=14&satkey=11929788>.
Hartman et al, "An Adenoviral vaccine encoding full-length inactivated human Her2 exhibits potent immunogenicity and enhanced therapeutic efficacy without oncogenicity" (2010) Clin Cancer Res 16(5).
Luo et al. "A protocol for rapid generation of recombinant adenoviruses using the AdEasy system" (2007) Nature Protocols 2:1236.
Ren et al. "Polyclonal Her2-specific antibodies induced by vaccination mediate receptor internalization and degradation in tumor cells" (2012) Breast Cancer Research 14:R89.
Schoeberl, Birgit et al. "An ErbB3 Antibody, MM-121, Is Active in Cancers with Ligand-Dependent Activation" (2010) Cancer Research: 70(6): 2485-2494.

(Continued)

Primary Examiner — Peter J Reddig
(74) Attorney, Agent, or Firm — Andrus Intellectual Property Law, LLP

(57) ABSTRACT

Methods of reducing the likelihood of a cancer or precancer developing resistance to a cancer therapeutic or prevention agent are provided herein. The methods include administering the cancer therapeutic or prevention agent and a vaccine comprising a polynucleotide encoding a polypeptide whose expression or activation is correlated with development of resistance of the cancer or precancer to the cancer therapeutic or prevention agent to a subject. The vaccine may include a polynucleotide encoding a HER3 polypeptide. Methods of using the vaccine including the polynucleotide encoding the HER3 polypeptide to treat a cancer or precancer are also provided.

16 Claims, 13 Drawing Sheets

(56) References Cited

OTHER PUBLICATIONS

Yoo, Ji Young et al. "Downregulation of ErbB3 Expression by Adenovirus Expressing ErbB3 Specific shRNA Enhances Antitumor Efficacy through Apoptosis Induction" (2009) Molecular Therapy: 17(Suppl. 1): S106.
Extended European Search Report for European Patent Application No. 13738296.6 dated Nov. 9, 2015 (10 pages).
International Search Report and Written Opinion for PCT/US2013/022396 dated May 3, 2013 (13 pages).
International Search Report and Written Opinion for PCT/US2015/039359 dated Oct. 7, 2015 (15 pages).
International Search Report and Written Opinion for PCT/US2015/039367 dated Oct. 15, 2015 (13 pages).

* cited by examiner

Fig. 1D

| HER3-VIA Antibody epitopes ||
|---|---|
| Epitope(s) position | Protein region |
| 101-111 | ECD |
| 153-167 | ECD |
| 185-191 | ECD |
| 209-223 | ECD |
| 369-375 | ECD |
| 501-511 | ECD |
| 589-599 | ECD |
| 649-663 | TM |
| 681-691 | ICD |
| 865-875 | ICD |
| 881-895 | ICD |
| 901-915 | ICD |
| 981-988 | ICD |
| 1037-1051 | ICD |
| 1105-1119 | ICD |
| 1153-1163 | ICD |
| 1249-1255 | ICD |
| 1268-1279 | ICD |

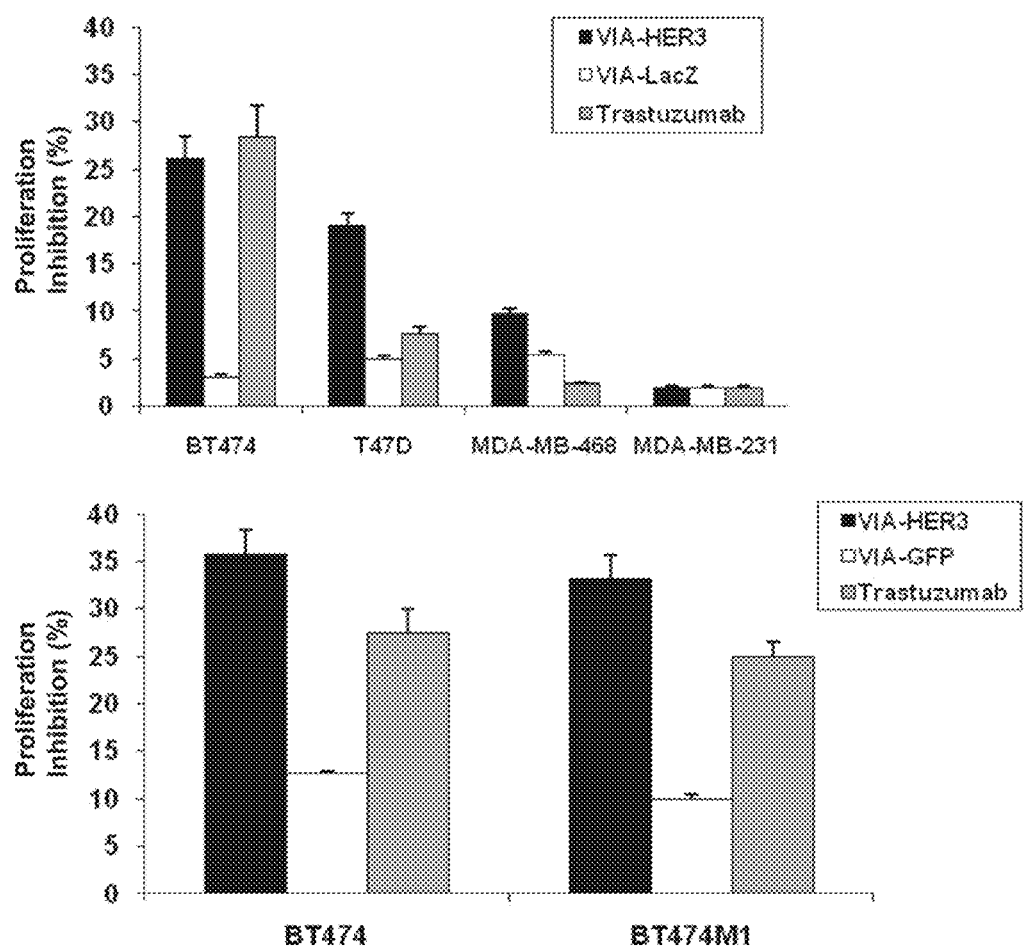

Day -2, 17ß-Estradiol pellet
Day 0, Tumor implantation
Day 14-33, Injection of HER3-VIA or GFP-VIA

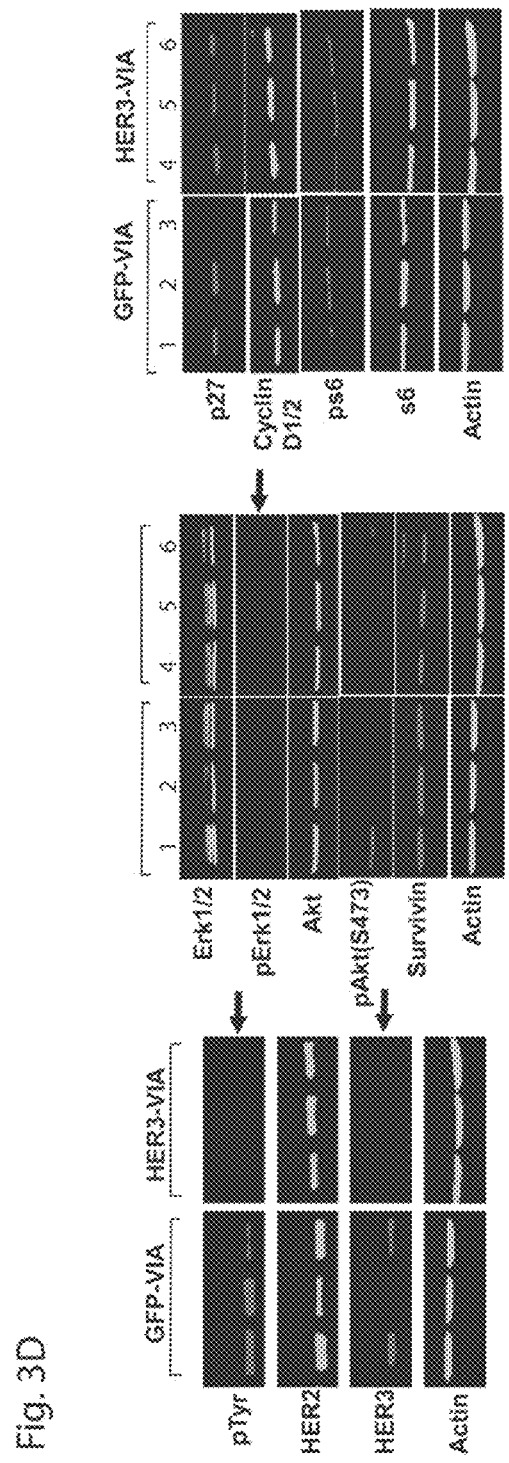

SEQUENCE LISTING

```
<160> NUMBER OF SEQ ID NOS: 26

<210> SEQ ID NO 1
<211> LENGTH: 331
<212> TYPE: PRT
<213> ORGANISM: Homo sapiens
<220> FEATURE:
```

<221> NAME/KEY: misc_feature
<223> OTHER INFORMATION: Human HER3 Protein amino acid sequence

<400> SEQUENCE: 1

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Phe
                325                 330
```

<210> SEQ ID NO 2
<211> LENGTH: 1342
<212> TYPE: PRT
<213> ORGANISM: Homo sapiens
<220> FEATURE:
<221> NAME/KEY: misc_feature
<223> OTHER INFORMATION: Human HER3 Protein Precursor amino acid sequence

<400> SEQUENCE: 2

```
Met Arg Ala Asn Asp Ala Leu Gln Val Leu Gly Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
                100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
                180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
    355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415
```

```
Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
    530                 535                 540

His Glu Ala Glu Cys Phe Ser Cys His Pro Glu Cys Gln Pro Met Gly
545                 550                 555                 560

Gly Thr Ala Thr Cys Asn Gly Ser Gly Ser Asp Thr Cys Ala Gln Cys
            565                 570                 575

Ala His Phe Arg Asp Gly Pro His Cys Val Ser Ser Cys Pro His Gly
        580                 585                 590

Val Leu Gly Ala Lys Gly Pro Ile Tyr Lys Tyr Pro Asp Val Gln Asn
    595                 600                 605

Glu Cys Arg Pro Cys His Glu Asn Cys Thr Gln Gly Cys Lys Gly Pro
610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
            645                 650                 655

Met Met Leu Gly Gly Thr Phe Leu Tyr Trp Arg Gly Arg Arg Ile Gln
        660                 665                 670

Asn Lys Arg Ala Met Arg Arg Tyr Leu Glu Arg Gly Glu Ser Ile Glu
    675                 680                 685

Pro Leu Asp Pro Ser Glu Lys Ala Asn Lys Val Leu Ala Arg Ile Phe
690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
            725                 730                 735

Ile Pro Val Cys Ile Lys Val Ile Glu Asp Lys Ser Gly Arg Gln Ser
        740                 745                 750

Phe Gln Ala Val Thr Asp His Met Leu Ala Ile Gly Ser Leu Asp His
    755                 760                 765

Ala His Ile Val Arg Leu Leu Gly Leu Cys Pro Gly Ser Ser Leu Gln
770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Asn Trp Gly Val
            805                 810                 815

Gln Ile Ala Lys Gly Met Tyr Tyr Leu Glu Glu His Gly Met Val His
        820                 825                 830

Arg Asn Leu Ala Ala Arg Asn Val Leu Leu Lys Ser Pro Ser Gln Val
```

```
                    835              840              845
Gln Val Ala Asp Phe Gly Val Ala Asp Leu Leu Pro Pro Asp Lys
    850              855              860
Gln Leu Leu Tyr Ser Glu Ala Lys Thr Pro Ile Lys Trp Met Ala Leu
865              870              875              880
Glu Ser Ile His Phe Gly Lys Tyr Thr His Gln Ser Asp Val Trp Ser
                885              890              895
Tyr Gly Val Thr Val Trp Glu Leu Met Thr Phe Gly Ala Glu Pro Tyr
                900              905              910
Ala Gly Leu Arg Leu Ala Glu Val Pro Asp Leu Leu Glu Lys Gly Glu
                915              920              925
Arg Leu Ala Gln Pro Gln Ile Cys Thr Ile Asp Val Tyr Met Val Met
    930              935              940
Val Lys Cys Trp Met Ile Asp Glu Asn Ile Arg Pro Thr Phe Lys Glu
945              950              955              960
Leu Ala Asn Glu Phe Thr Arg Met Ala Arg Asp Pro Pro Arg Tyr Leu
                965              970              975
Val Ile Lys Arg Glu Ser Gly Pro Gly Ile Ala Pro Gly Pro Glu Pro
                980              985              990
His Gly Leu Thr Asn Lys Lys Leu Glu Glu Val Glu Leu Glu Pro Glu
                995             1000             1005
Leu Asp Leu Asp Leu Asp Leu Glu Ala Glu Glu Asp Asn Leu Ala
    1010             1015             1020
Thr Thr Thr Leu Gly Ser Ala Leu Ser Leu Pro Val Gly Thr Leu
    1025             1030             1035
Asn Arg Pro Arg Gly Ser Gln Ser Leu Leu Ser Pro Ser Ser Gly
    1040             1045             1050
Tyr Met Pro Met Asn Gln Gly Asn Leu Gly Gly Ser Cys Gln Glu
    1055             1060             1065
Ser Ala Val Ser Gly Ser Ser Glu Arg Cys Pro Arg Pro Val Ser
    1070             1075             1080
Leu His Pro Met Pro Arg Gly Cys Leu Ala Ser Glu Ser Ser Glu
    1085             1090             1095
Gly His Val Thr Gly Ser Glu Ala Glu Leu Gln Glu Lys Val Ser
    1100             1105             1110
Met Cys Arg Ser Arg Ser Arg Ser Arg Ser Pro Arg Pro Arg Gly
    1115             1120             1125
Asp Ser Ala Tyr His Ser Gln Arg His Ser Leu Leu Thr Pro Val
    1130             1135             1140
Thr Pro Leu Ser Pro Pro Gly Leu Glu Glu Glu Asp Val Asn Gly
    1145             1150             1155
Tyr Val Met Pro Asp Thr His Leu Lys Gly Thr Pro Ser Ser Arg
    1160             1165             1170
Glu Gly Thr Leu Ser Ser Val Gly Leu Ser Ser Val Leu Gly Thr
    1175             1180             1185
Glu Glu Glu Asp Glu Asp Glu Glu Tyr Glu Tyr Met Asn Arg Arg
    1190             1195             1200
Arg Arg His Ser Pro Pro His Pro Pro Arg Pro Ser Ser Leu Glu
    1205             1210             1215
Glu Leu Gly Tyr Glu Tyr Met Asp Val Gly Ser Asp Leu Ser Ala
    1220             1225             1230
Ser Leu Gly Ser Thr Gln Ser Cys Pro Leu His Pro Val Pro Ile
    1235             1240             1245
```

| | | | | | | | | | | |
|---|---|---|---|---|---|---|---|---|---|---|
| Met | Pro | Thr | Ala | Gly | Thr | Thr | Pro | Asp | Glu | Asp | Tyr | Glu | Tyr | Met |
| | 1250 | | | | 1255 | | | | | 1260 |

| Asn | Arg | Gln | Arg | Asp | Gly | Gly | Pro | Gly | Gly | Asp | Tyr | Ala | Ala |
|---|---|---|---|---|---|---|---|---|---|---|---|---|---|
| | 1265 | | | | 1270 | | | | 1275 |

| Met | Gly | Ala | Cys | Pro | Ala | Ser | Glu | Gln | Gly | Tyr | Glu | Glu | Met | Arg |
|---|---|---|---|---|---|---|---|---|---|---|---|---|---|---|
| | 1280 | | | | 1285 | | | | | 1290 |

| Ala | Phe | Gln | Gly | Pro | Gly | His | Gln | Ala | Pro | His | Val | His | Tyr | Ala |
|---|---|---|---|---|---|---|---|---|---|---|---|---|---|---|
| | 1295 | | | | | 1300 | | | | 1305 |

| Arg | Leu | Lys | Thr | Leu | Arg | Ser | Leu | Glu | Ala | Thr | Asp | Ser | Ala | Phe |
|---|---|---|---|---|---|---|---|---|---|---|---|---|---|---|
| | 1310 | | | | 1315 | | | | | 1320 |

| Asp | Asn | Pro | Asp | Tyr | Trp | His | Ser | Arg | Leu | Phe | Pro | Lys | Ala | Asn |
|---|---|---|---|---|---|---|---|---|---|---|---|---|---|---|
| | 1325 | | | | 1330 | | | | | 1335 |

| Ala | Gln | Arg | Thr |
|---|---|---|---|
| | 1340 |

<210> SEQ ID NO 3
<211> LENGTH: 4975
<212> TYPE: DNA
<213> ORGANISM: Homo sapiens
<220> FEATURE:
<221> NAME/KEY: misc_feature
<223> OTHER INFORMATION: Human HER3 mRNA sequence

<400> SEQUENCE: 3

```
ctctcacaca cacacacccc tcccctgcca tccctcccog gactccggct ccggctccga      60
ttgcaatttg caacctccgc tgccgtcgcc gcagcagcca ccaattcgcc agcggttcag     120
gtggctcttg cctcgatgtc ctagcctagg gccccgggg ccggacttgg ctgggctccc     180
ttcaccctct gcggagtcat gagggcgaac gacgctctgc aggtgctggg cttgcttttc     240
agcctggccc ggggctccga ggtgggcaac tctcaggcag tgtgtcctgg gactctgaat     300
ggcctgagtg tgaccggcga tgctgagaac caataccaga cactgtacaa gctctacgag     360
aggtgtgagg tggtgatggg gaaccttgag attgtgctca cgggacacaa tgccgacctc     420
tccttcctgc agtggattcg agaagtgaca ggctatgtcc tcgtggccat gaatgaattc     480
tctactctac cattgcccaa cctccgcgtg gtgcgaggga cccaggtcta cgatgggaag     540
tttgccatct tcgtcatgtt gaactataac accaactcca gccacgctct gcgccagctc     600
cgcttgactc agctcaccga gattctgtca ggggtgtttt atattgagaa gaacgataag     660
ctttgtcaca tggacacaat tgactggagg gacatcgtga gggaccgaga tgctgagata     720
gtggtgaagg acaatggcag aagctgtccc ccctgtcatg aggtttgcaa ggggcgatgc     780
tggggtcctg atcagaaga ctgccagaca ttgaccaaga ccatctgtgc tcctcagtgt     840
aatggtcact gctttgggcc caaccccaac cagtgctgcc atgatgagtg tgccgggggc     900
tgctcaggcc ctcaggacac agactgcttt gcctgccggg acttcaatga cagtggagcc     960
tgtgtacctc gctgtccaca gcctcttgtc tacaacaagc taactttcca gctggaaccc    1020
aatcccaca ccaagtatca gtatggagga gtttgtgtag ccagctgtcc cataactttt    1080
gtggtggatc aaacatcctg tgtcagggcc tgtcctcctg acaagatgga agtagataaa    1140
aatgggctca gatgtgtga gccttgtggg ggactatgtc ccaaagcctg tgaggaaca     1200
ggctctggga gccgcttcca gactgtggac tcgagcaaca ttgatggatt tgtgaactgc    1260
accaagatcc tgggcaacct ggactttctg atcaccggcc tcaatggaga ccctggcac     1320
aagatccctg ccctggaccc agagaagctc aatgtcttcc ggacagtacg ggagatcaca    1380
```

```
ggttacctga acatccagtc ctggccgccc cacatgcaca acttcagtgt ttttccaat      1440
ttgacaacca ttggaggcag aagcctctac aaccggggct tctcattgtt gatcatgaag     1500
aacttgaatg tcacatctct gggcttccga tccctgaagg aaattagtgc tgggcgtatc     1560
tatataagtg ccaataggca gctctgctac caccactctt tgaactggac caaggtgctt     1620
cgggggccta cggaagagcg actagacatc aagcataatc ggccgcgcag agactgcgtg     1680
gcagagggca aagtgtgtga cccactgtgc tcctctgggg gatgctgggg cccaggccct     1740
ggtcagtgct tgtcctgtcg aaattatagc cgaggaggtg tctgtgtgac ccactgcaac     1800
tttctgaatg gggagcctcg agaatttgcc catgaggccg aatgcttctc ctgccacccg     1860
gaatgccaac ccatgggggg cactgccaca tgcaatggct cgggctctga tacttgtgct     1920
caatgtgccc attttcgaga tgggcccac tgtgtgagca gctgccccca tggagtccta     1980
ggtgccaagg gcccaatcta caagtaccca gatgttcaga atgaatgtcg gccctgccat     2040
gagaactgca cccaggggtg taaaggacca gagcttcaag actgtttagg acaaacactg     2100
gtgctgatcg gcaaaaccca tctgacaatg gctttgacag tgatagcagg attggtagtg     2160
attttcatga tgctgggcgg cactttctc tactggcgtg ggcgccggat tcagaataaa      2220
agggctatga ggcgatactt ggaacgggt gagagcatag agcctctgga ccccagtgag      2280
aaggctaaca aagtcttggc cagaatcttc aaagagacag agctaaggaa gcttaaagtg     2340
cttggctcgg gtgtctttgg aactgtgcac aaaggagtgt ggatccctga gggtgaatca     2400
atcaagattc cagtctgcat taaagtcatt gaggacaaga gtggacggca gagttttcaa     2460
gctgtgacag atcatatgct ggccattggc agcctggacc atgcccacat tgtaaggctg     2520
ctgggactat gcccagggtc atctctgcag cttgtcactc aatatttgcc tctgggttct     2580
ctgctggatc atgtgagaca caccggggg gcactgggc cacagctgct gctcaactgg       2640
ggagtacaaa ttgccaaggg aatgtactac cttgaggaac atggtatggt gcatagaaac     2700
ctggctgccc gaaacgtgct actcaagtca cccagtcagg ttcaggtggc agattttggt     2760
gtggctgacc tgctgcctcc tgatgataag cagctgctat acagtgaggc caagactcca     2820
attaagtgga tggcccttga gagtatccac tttgggaaat acacacacca gagtgatgtc     2880
tggagctatg gtgtgacagt ttgggagttg atgaccttcg gggcagagcc ctatgcaggg     2940
ctacgattgg ctgaagtacc agacctgcta gagaaggggg agcggttggc acagccccag     3000
atctgcacaa ttgatgtcta catggtgatg gtcaagtgtt ggatgattga tgagaacatt     3060
cgcccaacct ttaaagaact agccaatgag ttcaccagga tggcccgaga cccaccacgg     3120
tatctggtca taagagaga gagtgggcct ggaatagccc ctgggccaga gcccatggt       3180
ctgacaaaca agaagctaga ggaagtagag ctggagccag aactagacct agacctagac     3240
ttggaagcag aggaggacaa cctggcaacc accacactgg gctccgccct cagcctacca     3300
gttgaaacac ttaatcggcc acgtgggagc cagagccttt taagtccatc atctggatac     3360
atgcccatga accagggtaa tcttggggg tcttgccagg agtctgcagt ttctgggagc      3420
agtgaacggt gccccgtcc agtctctcta cacccaatgc cacggggatg cctggcatca     3480
gagtcatcag aggggcatgt aacaggctct gaggctgagc tccaggagaa agtgtcaatg     3540
tgtagaagcc ggagcaggag ccggagccca cggccacgcg agatagcgc ctaccattcc      3600
cagcgccaca gtctgctgac tcctgttacc ccactctccc cacccgggtt agaggaagag     3660
gatgtcaacg ttatgtcat gccagataca cacctcaaag gtactccctc ctcccgggaa      3720
ggcacccttt cttcagtggg tctcagttct gtcctgggta ctgaagaaga agatgaagat    3780
```

```
gaggagtatg aatacatgaa ccggaggaga aggcacagtc cacctcatcc ccctaggcca    3840
agttcccttg aggagctggg ttatgagtac atggatgtgg ggtcagacct cagtgcctct    3900
ctgggcagca cacagagttg cccactccac cctgtaccca tcatgccacc tgcaggcaca    3960
actccagatg aagactatga atatatgaat cggcaacgag atggaggtgg tcctgggggt    4020
gattatgcag ccatggggc  ctgcccagca tctgagcaag ggtatgaaga gatgagagct    4080
tttcaggggc ctggacatca ggcccccat  gtccattatg cccgcctaaa aactctacgt    4140
agcttagagg ctacagactc tgcctttgat aaccctgatt actggcatag caggctttc     4200 cccaaggcta atgcccagag aacgtaactc ctgctccctg tggcactcag ggagcattta    4260
atggcagcta gtgcctttag agggtaccgt cttctcccta ttccctctct ctcccaggtc    4320
ccagcccctt ttccccagtc ccagacaatt ccattcaatc tttggaggct tttaaacatt    4380
ttgacacaaa attcttatgg tatgtagcca gctgtgcact ttcttctctt tcccaacccc    4440
aggaaaggtt ttccttattt tgtgtgcttt cccagtccca ttcctcagct tcttcacagg    4500
cactcctgga gatatgaagg attactctcc atatcccttc ctctcaggct cttgactact    4560
tggaactagg ctcttatgtg tgcctttgtt tcccatcaga ctgtcaagaa gaggaaaggg    4620
aggaaaccta gcagaggaaa gtgtaatttt ggtttatgac tcttaacccc ctagaaagac    4680
agaagcttaa aatctgtgaa gaaagaggtt aggagtagaa attgattact atcataattc    4740
agcacttaac tatgagccag gcatcatact aaacttcacc tacattatct cacttagtcc    4800
tttatcatcc ttaaaacaat tctgtgacat acatattatc tcattttaca caaagggaag    4860
tcgggcatgg tggctcatgc ctgtaatctc agcactttgg gaggctgagg cagaaggatt    4920
acctgaggca aggagtttga gaccagctta gccaacatag taagaccccc atctc          4975
```

<210> SEQ ID NO 4
<211> LENGTH: 30237
<212> TYPE: DNA
<213> ORGANISM: Homo sapiens
<220> FEATURE:
<221> NAME/KEY: misc_feature
<223> OTHER INFORMATION: Human HER3 DNA sequence

<400> SEQUENCE: 4

```
tttttttatt gataattctt gggtgttcct cacagagggg gatttggcag ggtcatggga     60
caatagtgga ggggaaggtca gcagataaac aagtgaacaa aggtctctgg tttttcctagg   120 cagaggaccc tgcggccttc cgcagtgttt gtgtccctga ttacttgaga ttggggagtg    180
gtgatgactc ttaatgagca tgctgccttc aagcatctgt ttaacaaagc acatcttgca    240
ccgcccttaa tccatttaac cctgagtgga cacagcacat gtttcagaga gcacagggtt    300
gggggtaagg tcacagatca acaggatccc aaggcagaag aattttttctt agtgcagaac    360 aaaatgaaaa gtctcccatg tctacttctt tctacacaga cacggcaacc atccgatttc    420
tcaatctttt ccccacctt  cccgcctttc tattccacaa agccgccatt gtcatcctgg    480
cccgttctca atgagctgtt gggtacacct cccagacggg gtggtggccg gcagaggtg     540 cccctcacct cccagacggg gcggctgccg gggcgggggg ctgaccccc  cacctcccctc   600 ccggacgggg cggctggccg ggcgggggc  tgacccccca acctccctcc ccgacggggc    660
ggctggccgg gcggggggct gacccccca  cctccctcct ggacggggcg gctgatcggg    720
cgaggggctg acccccccat ctccctcccg gatggggtgg ctgccggggcg gagactctcc    780 tcacttccca gatggggtgg ctgccggggcg gagaggctcc tcacttctca gacggggcag    840
```

```
ctgccggacg gaggggctcc tcacttctca gacggggtgg ttgccaggca gagggtctcc    900
tcacttctca gacggggcgg ccgagcagag acgctcttca cctcccagac ggggtcgctg    960
ccgggcagag gcgctcctca tatcccagat ggggcggcgg ggcagaggcg ctccccacat   1020
ctcagacaat gggcggccgg gcagagacgc tcctcacttc ctagatgtga tggcggccgg   1080
gaagaggcgc tcctcacttc ctagatggga tggcggcagg gcggagacgc tcctcacttt   1140
ccagactggg cagccaggca gaggggctcc tcacatccca gacgatgggc ggccaggcag   1200
agacactcct cacttcccag acggggtggc ggccgggcag aggctgcaat ctcagcactt   1260
tgggaggcca aggcaggcgg ctgggaggtg taggttgtag tgagccgaga tcacgccact   1320
gcactccagc ctgggcacca ttgagcactg agtgaacgag actccgtctg caatcccggc   1380
acctcgggag gccgaggctg gcggatcact cgcggttagg ggctggagac cggcccggcc   1440
aacacagcga aaccccgtct ccaccaaaac cagtcaggcg tggcggcgcg tgcctgcaat   1500
cgcaggcact cggcaggctg aggcaggaga atcaggcagg gaggttgcag tgagccgaga   1560
tggcagcagt acagtccagc ttcggctccg catgagaggg agaccgtgga aagagaggga   1620
gaccgtgggg agagggagag ggggaggggg aggggaggg ggagggacca atcaacagtc   1680
ttataagtag atacaacagt gtataaacaa ggaaaccaag gaagattttt ctccttcaga   1740
actcggaccc tgaataccag gttgagctgg agctgagtga gtaataaaat gaaaggccct   1800
ttaatgtggg ggagggtagg taggagtgga gacccttaag tagtatcagc actgttgtct   1860
gatgggagtg tgaatctgaa cacatgaagc tccagtctca gtagaacagt aagaaatcct   1920
aagtaaggcc aggcatggtt cacatctgaa atcctaacaa tttgggtaaa ctgaggtgga   1980
aggattgcag aggccaggag ttcaagacca gcttgggcaa catagccaga cccccacccc   2040
cacccccgca tctccatatc atacaaaaat aataaagaaa tcctaggtaa ggccagatgg   2100
taaggccagg tgtggtggct catgcctgta atcccagcac tttgggaggc cgaggtgggt   2160
ggattgccca aggtcaggag ttcaagacca gcttggtcaa cacagtgaaa cccgtctct    2220 actaaaaata caaaaattag ctaggtgttg tggcaggcac ctgtaatctc aactactcag   2280
gaggctgagg caggagaata gcttgaaccc aagaggcaga ggttgcagtg agccaagatc   2340
gagccattgc actccagcct gggcaccaaa agcgaaactc aggagaatgc cttgaaccca   2400
ggaggcagag gttgcagtga gctgagatca cgccattgca ctccagcctg ggtgacagag   2460
cgagactcca tctcaaaaac aaacaaacaa ataaacaaag tagccagaca ttttggtgcc   2520
cacctgtaga ctcagttact agggaggctg aagtgggaga atcacctgag cctgggaagt   2580
tgaggctgct gtgagccatg attgcaccac tgcactccag cctgggtgac agagggagat   2640
cctgtctcaa aaaaggaaa aaaagccagg tgtggtggct cacacctgta atcccagcac   2700
tttgggaggc tgaggtgggt ggatcacctg aggtcaggaa ttagagacta gtctggccat   2760
cacagtgaaa ccccatctct actaaaaata caaaaaatta gccgggcttg gtggcgcacg   2820
ccttgtagcc ccagctactt ggaagcctga ggcaggagaa tcacttgaac tcagtagtga   2880
gctgagatca ggccactgca ctccagcctg ggtgacagaa acagaacaag attccgtgtc   2940
aaaaaaaaaa aagcaacaga ccagaaggcc atgaggtcaa acaaaacaat gttttgtttt   3000
tgttttgaga tggcgtctca ctctgtcgcc caagctggag tgcagtgatg caatctcagc   3060
tcactgcaac ctccacctcc cgggttcaag cgattctcct gcctcagtct cctaagtagc   3120
tgggattaca ggtgcccacc atcatgccca gctaattttt gtatttttag tagagacggt   3180
```

```
gtttcactat gttgactagg ctggtctcga actcctgacc tcaagtgatc tgcccgcctc    3240
ggcctcccaa agtgctggga ttacaggcat gagccaccgc gcccagccga atgttttgtt    3300
ttttaagatg gaagatatcc cagcactttg gcaggctgaa gcaggtggat cattccagct    3360
tgggcaacaa gagcgaaact ctgtctcaaa aaaaaaaaaa aagaaaagaa aaaaaagag     3420 agaaagaaac cctaggtaaa agtctgagcc ccacctccca atcacctgat cacctcaacc    3480
actgtcacca ggtggatgac cttggagagg tcacacactt ctagttctgt aaaatgggga    3540
gttatattgc ctaaatcata taattttttat gttaagtgac acattctcta aggcactaag   3600
tttgaggaca tactttgtaa atgaaatgat atatggaaat gtttgtatat gttaatggtt    3660
ttgttgttgc tattattatt atgactacta tacacatggt ctggagaaag ccaacctccc    3720
caaagcggag attctccagt agagaacagg ccctctaggt tgcatatcaa tagggagcat    3780
gtttaaggaa tgttagccgg tagtctttgc taggtgtgag gggtgaaatt tttctttatc    3840
aaggctcaac tgttttcgaa gtcttcaggc ttgaagttct ggagaaaaca actaggctct    3900
ccgggcgaga tcccgaatac cagtttaagg gatttgaaat gcaaggccgt ctgggactcc    3960
actgccacgg atgggcacca ggcggcgccg gtcggatccg tcccgggact agcagggctt    4020
tgggcagcaa cccgcaggga gcccgaccgc ctctggccag gtccgggcag ctggtggggg    4080
aggttccaga ggtccacgcc attcgtggac gcagtctcta gtgtcctctc cgcgtcccac    4140
ttcactgccc catccccttt cctgcgagag cctggacttg gaaggcacct gggagggtgt    4200
aagcgccttg gtgtgtgccc atctgggtcc ccagaagagc ggcgggaact gcggccgccc    4260
ggacggtgcg gccagactcc agtgtggaag gggaggcagc tgttctccca ggcggccgtg    4320
gggggcagca gaggggacgg cgacaggtgc gggagcccct cccggggtag aagtggaaag    4380
gcgggctccg gggtctgttc ccaggctgga aaccaccccc gcccccatc caaatccccg     4440 ggagaggccc ggccggcgcc gggtctggag gaggaagcgg ccagagacag tgcaatttca    4500
cgcggtctct gtggctcggg ttcctgggct gggtggatga attatggggt ttcgagtctg    4560
ggagaaactg aggtggcctg gacgtgaggc aaaaaacacc ctcccccctca aaaacacaca   4620 gagagaaata ttcacattct gagagaaaat ccaccaagtg aaccaaccgg ctaggggagt    4680
tgagtgattt ggttaatggg cgaggccaac tttcaggggg cagggctttg gagagctttc    4740
cactccctca ttcattaccc ttccctggat ctggggggctt tcggaatctc gacctcccct   4800
tggcctatct cctgcagaaa aattagggtg agccccatcc tcgatctgct ccgccaagtt    4860
gcgggaccgc ggggcgtggc acgctcgggg caggcggtcc gaggctccgc aatccctact    4920
ccagcctcgc gcgggagggg gcgcggccgt gactcacccc cttccctctg cgttcctccc    4980
tccctctctc tctctctctc acacacacac cccctccccc tgccatccct ccccggactc    5040
cggctccggc tccgattgca atttgcaacc tccgctgccg tcgccgcagc agccaccaat    5100
tcgccagcgg ttcaggtggc tcttgcctcg atgtcctagc ctaggggccc ccgggccgga    5160
cttggctggg ctcccttcac cctctgcgga gtcatgaggg cgaacgacgc tctgcaggtg    5220
ctgggcttgc ttttcagcct ggcccggggc tccgaggtgg gcaactctca ggcaggtaag    5280
tggcgcgaga gcaccggcgg gctcggcacc tgggagccgg aacccagtgc gcgcagcctc    5340
ggagggtatg ggcacggtct caggcggcgc ggggttgtgg gtgctgcccc cggtttgcca    5400
ggaccacctg ggagaggggc ggtcaggctc gggttatcgg cgtggtccgg ccgagggcgg    5460
cattccggga ccctcacgcc acccttctcc agagcgtcgc cgaccctcta attggtctcc    5520
ccagaagagg ctgaggccga aacagtagtt cacacttctg aggggccctg cagggagggg    5580
```

```
agcagggaac ttcattctgt aaacaggagg tgcttggagg tggggccctt ggcgggaagg    5640
gtctcggttt gctcgccaac cccctgcccc ccacccgcgc cgatttcagc taccccctagt   5700 ttcgttgttt tgccgacagg gcggagctac agaaggttgg aggggggttgt tgttctctgg   5760 tgttggaaaa acaggagcgg cacctcctct tccgtgagtg agcctgccct ggggaggtct    5820
gagattaacc agagggccaa gttcaggtga catcaggcag gaggcccaac agaggctggc    5880 gcccccttc ctcagtatag cagagcttaa gcaacatctc tttgtcaaga cccaggtcaa    5940
cacaactcat atttattgag catctactat acacaaggcc ctgggccagg agctgtaagg    6000
gcaaggatgt ccagcctctg gtcttttctc tccccaacct gaggatcaag agggcacctc    6060
tgctactttc taagcctcct gccttgggga gtccttcctg ggctcagctt gtgcctcccg    6120
cccccatttt gcttattgtc tgacactgtc tctaggaccc tagacagagc cccggattgc    6180
tcttctccag tcctcccccg actcccatgc tatctgagcc cacccctttg gggtgtctct    6240
gggaccgtgg acacctgagg actgaagttc tgtggatctc ctcccctccc ctcagatctc    6300
agcttggggt ttggcacagc cagggcccct tccccagtgt gggagtggaa gaaaccacct    6360
gtgcttccct cacagttgct gggcctaaat ttagatcctg gattttag atgtgaacac     6420 tcccagctgg tggagggggg tggtctgggg actggcgtgg gagggagcag tggagtgact    6480
gtataactgt cccatccaga ctcctgcaat cttcacccag aaaccaggaa gtaccagagt    6540
ctggccaccc tccctgggga ggcaggaggc aggcatggtt gggtctcttt acccttatc    6600 tgggtcctgc agcctctggg catccggccc tgtctcagtc cttctatagc ccctttgtcc    6660
tggctgtgat gggggtgggg gatgttggag gggaggcctc tggttgagga ggggctggag    6720
attctggctc tatcccaccc ctagtgctct ctaccaaagg agggcctgtg acactgcccc   6780
tccctatgct cccggttcct gggtacagca gggattttta tgattccctt cccctgccct   6840 gctcccaag ctgcctagct cctccccaga ggtgttgttt gtgctccctt cctgcccagg    6900
ccctttgccc cctgttttgtg taatatggac tttaccctca gggtagcagg gaactgggct   6960
acctctaaca ctgtagcctt ccaagcacag acacaaagtc tgcacaaaca cttatgggca   7020
cgtgggatag atggggccac ctgaaatact tcctgcaagg aaacccaact atagattcct    7080
gagccagcag gaccaatgtg tacgtgttcg tgtgtacatt gtgtgtgtat gtgtgtgccc    7140
acactactac ttccctgtgc agaaagcttg gctcctccct tatctgggga gaagtgttgg    7200
cactataact tgggaaaggg ggtatcctgc caggaagggg attggggtgg ggctgttcca    7260
gaaatgacta accttcctag tctctttcat ttcaacccaa ggaccctgga gttcccagct    7320
cctctggaac tagctctctt tgctgggact agccaacctt catggggagt gataaggagc    7380
cctccaaggt caagaagtca gactaggggt gtatgttata ggagggattg gggcctcacc    7440
agtctccctc cctccattcc cactgttgcc tcccactgag ctaccaccgc ctcagggaag    7500
ggtggctgga acaggtggta tctacccct actcccacc ccacacatgg tctttccctg     7560
aaccagagga aagagactgg ggtagggctt cagagtccag gacttcccat agcccgttgt    7620
ccaccacatt tgcaaagaag agtgaactcc caaggctgac atgccatgta cctctagtct    7680
aggctctccc ctagtgtggg tgaggattgc catggtgaaa gcttttttca tgaacctctt    7740
ctaacaatga aattgtgtgg aggctcaata tggggcatct gctactatct ctctccaggt    7800
tcctctgtat ttgctgaaaa atactctagg gctggaaagt gatgctgagg ttgctagagt    7860
gtgttgggat gggggagaga gtgagaagga aaccctgagt ttaggaaggc ggggaggcaa    7920
```

```
ctagctcctt atctttcagc tttaaagaca aagctcccat tgaccccccc tcaccccagc    7980
actgccagag ctccccctc tactgaggtc acttgtctga gcccaaggct tgagggtgga     8040
ggggagtgct gctgaggacg gggtgtctag ggacagggtg gggcagcccc cctcctggat    8100
agaatcgcct cattgtgggc tggactgtgg ccccaggcac tgcccccacc ctctgccccc    8160
atcccaccct cagtagacac aatagggggct gtgtactagt cccaaagaga tatttattcc   8220
aggacctaga gagaggcagg atgagggtag agaagtgagt gccctagttg gaggggagaa    8280
ggagggtaat caaagttgcg gccttttcct aacttctctt ttctagggag agaaacaaat    8340
tccctgtctt ccttctcagt taaccccctta gtacccaaaa gaagcacaga ggggtcccag   8400
gttgaaaaag gaaatctttt caccttccca ttcatggaat ggtaagggga ttctgagaag    8460 agaaaagct ctcaggccac tacagcttct gcctatcgct tgtgggaggg ttggaggcaa     8520
atgccatctg atcctgtcta atgtaactgg aagagggcaa ccaaggggt gatctttggg     8580 gatggcagat gggctgagaa tttgtgtcca gccctcagcc actcttccct ctgctttgaa    8640
cagtgtgtcc tgggactctg aatggcctga gtgtgaccgg cgatgctgag aaccaatacc    8700
agacactgta caagctctac gagaggtgtg aggtggtgat ggggaacctt gagattgtgc    8760
tcacgggaca caatgccgac ctctccttcc tgcaggttag tgagcccacc ctccttcctc    8820
aacctgctcc tctttattct cccctagaac cctccttcct tcttcagggc taccttctgc    8880
tggagttcac ccttcctaag actcaggagt tcctaagatt caaaaccgtg tatttatggg    8940
gacagtggct gtcatctggg acctatggtc tcactgttgt agccagggat atatagggg     9000 cagggtcagg ggcaggtggt gttctgtgga tagtgcaagg tcagcaggga ctagtgcaga    9060
gagaaacctg aggaccaaga ggttacctgg ggagatgagg aaggggccct actggtatga    9120
ggcactttga ggagaaagct gcctgtcttc actcccagaa gtgacacagc agtgtgacac    9180
agtctactcc ctactcccaa ataggaatta gcaagagtta aggccaggtg cagtggctca    9240
tgcctgtaat cccagcactt tgggaggcca aggaaggcag atcacttgag gtcaggagtt    9300
caagaccagc ctgggcaatg tggtgaaacg ctgtctctac aaaaatacaa aaattagctg    9360
ggtatggtgg catgcacctg tagtcccagc tacttggagg gctgaggtgg gaggattgct    9420
tgagcccagg agtttgacgc tgcagtgagc gagattgtgc cactcgtaac agagcgagac    9480
cctgtctcac caaaaaaaaa aaaaaaggcc aagctcggat cacctgaggt caggagttcg    9540
agaccagcct gaccaacatg gaaaaccac atctctacta aaaatacaaa attagccagg    9600
tgtagtggca catgcctgta atcccagcta cttgggaggc tgcggcagga gaattgcttg    9660
aacccgggag gtggaggttg tggtgagcca agatcgcact attgtactcc agcctgggca    9720
acaagagcgt aactccgtct caaattttaa aaaaagaaa aaagaaagg aaagaaagaa      9780 ggaagaatta aaacagttaa agagtcttta atgcctgaag gaggagagga gattgagatt    9840
attttgccct gttgtctctc tcatttacat aatctgctct gtcacagtgg attcgagaag    9900
tgacaggcta tgtcctcgtg gccatgaatg aattctctac tctaccattg cccaacctcc    9960
gcgtggtgcg agggacccag gtctacgatg ggaagtttgc catcttcgtc atgttgaact    10020
ataacaccaa ctccagccac gctctgcgcc agctccgctt gactcagctc accggtcagt    10080
tcccgatggt tccttctggc ctcacccctc agccagccca agactggtac ctccttgatg    10140
atgacccaag actgctcact ctaagtgcct cttccaaggt gcctgtcacc ttggccgctg    10200
tctaaaggtc cattgctccc taagcaatag agggcccca gtaggggag ctaggggcat      10260 ctgctccagg gaaaggaacc ctgtgtcctt gtggggctgg agtcagagct ggatctgtta    10320
```

```
accgtttttc taatttcaaa gtacagtgta ccggaggcca ggcctgatgg cttacacctg    10380
taatcccagc attttgggag gccaaggagg gcagatcact tgagatcagg agtttgagac    10440
cagcctggcc aacatggcga aaccctgtct ctactaaaaa tacaaaaaaa taaaataaaa    10500
taaaaaatta gctggctata gtggtgcgca cctgtaatcc cagctgttca tgaggctgag    10560
gcaggagact cgcttgaacc tgggaggtgg aggttgcagt gagctgagat tgcaccactg    10620
cactctagcg taagtgacag tgagactccg tctcaaaaaa aaaaaaaaaa aaaaaaaaaa    10680
gcctgggcgc ggtggctcac gcctgtaatc ccagcacttt gggaggccaa ggcaggtgga    10740
tcacaaggtc aggagatcga gaccatcctg gctaacacgg tgaaacccccg tctctactaa    10800 aaatacaaaa aattagccag gtgtggtggc gggcgcctgt agtccgagct actcgggagg    10860
ctgaggcagg agaatggcgt gaacccggga ggcggagctt gcagtgagcc aagattgcac    10920
cactgcactc cagcctgggc gacagagcga gactccaaaa aaaaaaaaaa aaaaaaaac    10980 caaagtacag tatacctgga tgtccctcct tccctaggaa ttctaccttt actctcctaa    11040
accaaacccc tatgagctgg aggaatatag gggttaaaaa ccacctgtcc atcttctgct    11100
tctccatgtc ccagtcagtt ggaaaacata tgggcagggc ttggggagg gaatgttgag    11160 tcagaaatct ctccctctct ccctccccct cccccactag ctaaaccgga tctggacagg    11220
tgactgagga ggcaggagtt tcttttggcc tgactcctca tcttataaag ggagtcttct    11280
ctgcagctta gatttaattg gacctatctg tctgcctcat tctcccactc ctgagtctca    11340
ggtgtccttt tggatgggtg gagaggtaag gaagaggcgt tccgctgcgg cccttaaccc    11400
tgtcacttct ttccctacct cagagattct gtcaggggt gtttatattg agaagaacga    11460
taagctttgt cacatggaca caattgactg gagggacatc gtgagggacc gagatgctga    11520
gatagtggtg aaggacaatg gcagaagctg taagtggccg tgatcaagat tgctcccag    11580 tcccaccaaa ccagagtgac tcccttcttt ccatcatcct tacattcctg atctgaaccc    11640
gcctccccag tgaacaaaca cctcaggtcc ctgactcagc agcccaccag ggcagaccat    11700
tccagtctcc tggaatctaa accacagagg aggtgtttca agaaaaggag caggccgagc    11760
atggtggctc atgcctataa tcctggcact ttgggaagcc aaggtgggag gatcgcttga    11820
gcccaggagt ccaagaccag cctgagtaac atagcaaaaa atctacaaaa aattaaaaaa    11880
atcagacagg cgtagtggct cgcacctgta atcccggcta ctcaggaggc tgaggcagag    11940
gattgcttga gcccaggagg ctgcagctgc agtgagctgt gattgtgcca ttgtactcta    12000
gcctgggcaa cagagtgaga ccctgtctca aaaaaaaaa aaaaaatcc ctgagtacta    12060 agcagggaag ccagatcttt agactccaca tctgttactc gttccactag aatatactcc    12120
catttccttg gagcccacct tccctgacc attcacatgc atatattcct gcatatattc    12180
agtttgccca ggaggaacta agttcctggg ttgggactag gactaaggtt ggcatttgcc    12240
ccagtccctc cccttcagct gcccagtggg tggtgtggag gcgtggccgc gcccttgtt    12300 gacaggtcca cttgagccca gccctgctct ccaagggcag ggagggacac agccctggct    12360
ttttgcttcc cggggattgag gtgcctgtgt actgacatca tacccccgttg attaaaacaa    12420 gcctttctta gccctgatgg ccccttgtgt tgccttcctt cccaaccagg tcccccctgt    12480
catgaggttt gcaaggggcg atgctggggt cctggatcag aagactgcca gacatgtggg    12540
tttgaaattc cctccaaaaa cttcactcat acgctttcat atcccttcct ccccaagcct    12600
gggtcaacac tgtgggggag gcatgagcag tggcctcaga attcagtcct aggagcccta    12660
```

```
acagccatgc tttctctcct tccatagtga ccaagaccat ctgtgctcct cagtgtaatg    12720
gtcactgctt tgggcccaac cccaaccagt gctgccatga tgagtgtgcc ggggggctgct    12780 caggccctca ggacacagac tgctttgtat gtaccctttc cattgcctgg gttctgaaat    12840
tgggatgtgg cctttgagga ggaggtaggg gtacacacgt aacataaatc tgatgagcct    12900
ccttttttcc caggcctgcc ggcacttcaa tgacagtgga gcctgtgtac ctcgctgtcc    12960
acagcctctt gtctcaaaca agctaacttt ccagctggaa cccaatcccc acaccaagta    13020
tcagtatgga ggagtttgtg tagccagctg tccccgtaag tgtctgaggg aaggaacaa     13080 tgatcaacaa tagtagatcc aagattttag acaaaattgt ggaagggaaa aagaatccag    13140
ttggtgataa atagggagat tggtgaatgg ttatgatcat ctaaccactc cagtgagtga    13200
cccttacgtc cagtcctccc atgacttcag ctatcaccct tacttctgct ccttgtagca    13260
acaaatagtg aagagacttt tgaatctata gggcagcact taagggatct agggtggcag    13320
atggggacaa atccagtgca gagctggagg gagcctaggc ccagagcaag ggttccattg    13380
gtagctggtg atgttcctcc ctcatctcta atggtgtcct cctcctcttc cctagataac    13440
tttgtggtgg atcaaacatc ctgtgtcagg gcctgtcctc ctgacaagat ggaagtagat    13500
aaaaatgggc tcaagatgtg tgagccttgt gggggactat gtcccaaagg tgggtaggag    13560
atggtaagaa gttgtaaaga gacagccttt cctctgagcc tgcgcagacc accccactg     13620 aacctctctt acatttgcag cctgtgaggg aacaggctct gggagccgct tccagactgt    13680
ggactcgagc aacattgatg gatttgtgaa ctgcaccaag atcctgggca acctggactt    13740
tctgatcacc ggcctcaatg ggttagagat cctgccttcc ctccttagac cccagcccac    13800
gcacccctca cagttcattt cattggccaa aactttccta tgtggagctg actaggaatc    13860
aaagtcataa aattctagcc tgttacaaag gacctgaaag aatgcttaac acatcctcca    13920
tccaggcctt cggtcccctc aggaacatct ttgagcaatt caatatcgcc ctgccaagga    13980
acaagggaca ggaacaacat atcctccttc ttaaagtttt ctttttttatt ctttttttctt   14040 ttttgagata gggtcttgct ctgtcaccta ggctggagtg cagtggcgtg atctcgactc    14100
actgtagcct cgacctcctg ggctcaagtg atcccaagta gctgggacta taggcacaca    14160
ccatcatact tgactaattt ttttgtattt ttttgtagag acagggtctt gctatgttgc    14220
ccaggctgat ctcgaactcc tgtgctcaag caatcctccc atcttggcct cccaaagtgc    14280
tagggatcac agcacccaac ctccttctta aagttttgta aaagttcttc cttagatttg    14340
gataaaaatc tgtctccagg ctgggccccgg tggctcatgc ctataatccc agcactttgg    14400
gaggccgagg tgggcggatt acgaggtcag atcgagacca tcctggctaa catggtgaaa    14460
tgccatctct actaaaaaca caaaaattag ctgggtgtgg tggtgcacat gcctgtaatc    14520
ccagctactc aggaggctga ggcacagaaa tcacttgaac ccaggaggcg gaaattgcag    14580
tgaaccgaga ttacaccacc gcactccagc ctggcgacag agcgagactc tttctcaaaa    14640
aaaaaaaaga aagaaaaga aaattctgtc tccccatgac ttttagctgt tttcactcat     14700
tctgctcctt ggagcaaaaa gaacaaaggg actttctagt ctataggaca gcatttaaaa    14760
tgtgtgtgtg tgtgtaaaaa aacccacta tgaccacctg ttttttttttt tcctttaatt    14820 tttattttg acataatttt agatctacac taaagttgca agaatggtat aaaattcccc    14880
atatactttt tttttttttt taagacaaag tctcactctg ttcccaggc tagagtcag     14940 tggtgcaatc ttggctcact gcaacctccg cctcctctgc ctcccgggtt caagcaattc    15000
tcctgcctca gtctcctgag tagctggaat tataggtgtg tgccatcatg cccggctaat    15060
```

```
ttttgtattt ttagtagaga cagggtttca ccatgtaggc caggctggtc tcgaactcct   15120
gacctcaagt gatccacccg ccccagcttc ccaaagtgtt gggattacaa gtgtgagcca   15180
ccgcgtctgg cccccatac actcttttac ccagatcctc caaatgttaa cataccacat    15240
atggccgggc acagtggctc atgcctataa tcccagcact tgggaggct gaggcaggtg    15300
gatcactagg tgtggatcac gaggtcaaga gattgagacc atcctggcca acatggtgaa   15360
acctcatctc tactaaaaat acaaaaatta gctgggcgtg gtggtgtgcg cctgtagtcc   15420
cagttactca ggaggctgag gcaggagaat agcttgaacc tggcaggcag aggttgcagt   15480
gagccgagat cgcggcactg cactccagcc tggtgaaaga gcgagactct gtccccgcc    15540
aaaaaaaata ccacatacgc tttatcactt ctctctctct ctgtctctct ctacacacac   15600
acacacacac acaaaacaca tgctattgtt tttctggacc acgtgagggt aaattttcac   15660
acatggttct ttcttacccc tgttatattt cagcgtatat tccttaaaaa taatattttc   15720
ttacataacc acagcatagt tgtttgaatc ggaaaattaa cattaacaca aaatattatc   15780
taagctacag accttattca gatttcacta attgtcctcc taaggtttgg gatcatacat   15840
tacattcagt tatcgtggca cttcaatctc ctttataaca gctcctcagg ttttgtttat   15900
ctttcatgat attcttgatg agtatagatt aggtaatggg cagcatgttc ttcagtttgg   15960
attagtttga tgtgtcctca tgattagatt caagttttttg tagtttttttt ttgagacaag  16020
gtctggctct attgcccagg ctggaataca gtggcatgat ctcagctcac tgcaacctct   16080
gcctcccgtg ctcaagcgag cacctcagcc cctgagtag ctgggattac aggtgcatgc    16140
caccatgctt ggctaatttt atatatatat atatatat atatatataa ataatatata     16200
taaatataaa tatatatata taaataatat atataaatat atataaacat aaatattata   16260
tactatttat atatttatat atgtgtgtgt atatatatat atatttttttt ttttttttga  16320
gacggagtct cgctcttgtt gcccaggctg gagtgcagtg gcgtgatctc agctcacgca   16380
acctccacct ctcaggttca agccattctc tatagagaca gggttgcacc atgttgtcca   16440
ggatggtctc gaactcatga gctcaagtga tcctcctgtc tcagcctccc aaagtgctgg   16500
gattataggc atgcgccgct gccaggctgg agtttgataa gaacaccaca gaggctgtga   16560
gctcagggca tcctattgag gatgtacgtg atgttgattt gtcccagcac tcacaatgat   16620
gtctctggtc acttagttaa ggtgatatct gtcaggtttt tctactgtaa agttactatt   16680
tttccattca caattaatga atgtcttggg ataattgcct gaatcaatta ttgttatgat   16740
agttgccaaa tgataatttt ctaattccat tattccttct gcatttgttt gttggcattc   16800
tactgttagg aagagtcttt ccagctgagc acagtggctt atgcctgtaa tctcagccct   16860
tgggagcca gtgggaaaat tgcttgggcc caggagttca aggttacagt gagctatgat   16920
ggcactactg ctctccagcc agtgcactca ctctgcacaa cagagtgaga ccctgtctct   16980
taaaaaaaaa aaaaaaaaa ggccaggtgc agtggctcat gcctgtaatt ccagcacttt   17040
gggaggccga ggcgggcgga tcacaaggtc aggagttcaa gaccagcctg ccagcatgg    17100
tgaaaccctg tctctactaa aaatacaaaa aattagccag gcatggtggt gtgctcctgt   17160
attcccagct acttaggaag ctgaggcagg agaatcactt gaacccagga ggtggaggtt   17220
gcagtgagct gagattgctg ccactgtact ccagcctggg cgatagagca agactctgtc   17280
tcaaaaaaaa aaaaaaaaaa aaaaaaaaaa aaggtcttc ctttcctatt tactcttatg    17340
gatacttatt ttattctagt caatggttat aatcctttac aatcattatt tattttagcc   17400
```

```
agcccctcca agttggctcc tgtgttcttt gggctgtacc cttaattctt tgagtcttgt    17460
cttgtttgca caagatgctc tgggcttata ttatatttcc cccatcccag ccatttctcc    17520
aaggaatgtt tccttttagt ggagaatgat atttagaaac caaatgctga ggctgggtgt    17580
gctcattgcc attgagttat acctttacct tattgactgg tttctactgt tctattcaga    17640
gacccctggc acaagatccc tgccctggac ccagagaagc tcaatgtctt ccggacagta    17700
cgggagatca caggtgagtg gcagagagtt tgccctttct agaagaatag gtgaaccact    17760
ggcataaatt gcggtataac tacttgagaa aatcacgtcc caagttatag gggaggagcc    17820
aggagaaccc aagaaagaag aaggctccct gcccatatgc ctctctccaa cccctcaggt    17880
tacctgaaca tccagtcctg gccgccccac atgcacaact tcagtgtttt ttccaatttg    17940
acaaccattg gaggcagaag cctctacaag tgagtaaagg gtatggagga aatggcatct    18000
tcaggcaatg aagcctgtgt cataggcatt ctttagtaaa atacaaggca ctgtctcata    18060
cagcagtgcc tcaaaaccaa agggtttcag agtttcacga ggaaaaggca aaaggagggg    18120
gattccctct cagtggatct gactagcact gagcaaatt cttgactaac atgaatcctt    18180
tgaatagtta atgttccctt agtagtctct cctctcatcc tgtctcctta ttctcagccg    18240
gggcttctca ttgttgatca tgaagaactt gaatgtcaca tctctgggct tccgatccct    18300
gaaggaaatt agtgctgggc gtatctatat aagtgccaat aggcagctct gctaccaca    18360 ctctttgaac tggaccaagg tgcttcgggg cctacggaa gagcgactag acatcaagca    18420

taatcggccg cgcagagact gcggtgaggg aaagggtctg ctaggtggtg agaataggga    18480 gtcaggagg agagggctga aaggactatt ctgccctaga cgtgggagta gggttgaggg    18540
atggaaccaa ggagaagggg gctgttaggc tggaagcagt aacgaggaag aataatgaag    18600
agagggcttg ctgggagtcc tcagactcct ctcctaaccc accccttcct ttccagtggc    18660
agagggcaaa gtgtgtgacc cactgtgctc ctctggggga tgctggggcc caggccctgg    18720

tcagtgcttg tcctgtcgaa attatagccg aggaggtgtc tgtgtgaccc actgcaactt    18780

tctgaatggg tacagtaagg ggagccagtc aaggatgggt gggggtgggg ccctgcaatg    18840
gaactgttca ggtggcatac aataaaagtc tttagacagc ttctgcatg tgccttggtg    18900 ggattgaggt aggagacctg tggttgtgag atcggagcat gaaggtcagg acttggaagt    18960
gacccccccc tccctttatt ccccactaca gggagcctcg agaatttgcc catgaggccg    19020
aatgcttctc ctgccacccg gaatgccaac ccatggaggg cactgccaca tgcaatggct    19080
cggtatacta gtagcaccag gatctccaag ggagacagag aagggcaat acttggagca    19140

tctggggaat gatatggcta aggatagcac agagaggcca gataatgcta gggcctgcag    19200
atagaagatc ctgaatgtct gggttggtct tgctgggag gtatggaatt gaccttggga    19260

tctgattctt cctgaccttc tctcttccac tcagggctct gatacttgtg ctcaatgtgc    19320
ccatttccga gatgggcccc actgtgtgag cagctgcccc catggagtcc taggtgccaa    19380
gggcccaatc tacaagtacc cagatgttca gaatgaatgt cggccctgcc atgagaactg    19440
cacccagggg tcagtgatgg gataataagg agaggggtc aggtggaagg gtaggagcac    19500
agaactagag tgagggaagc agaaagaaga gagaggctgt gattcaagaa tcactcccag    19560
ctggccgggc gcagtggctc acacctgtaa tcccagcact gtgggaggcc gaggtggctg    19620
gatcacctga ggtcgggagt tcgagaccag cctgaccaat atggagaaac cctgtctcta    19680
ccaaaaattt aaaattagcc cggcgtgtg gcgcatgcct gtaatcccag ctacgcggga    19740
ggctgaggca ggagaatttc ttgaacccag gaggcagagg ttgcggtgag ctgagattgc    19800
```

```
atcattgtac tccagcctgg gcaacaagag tgaaactctg tctcaaaaaa aaaaaaagaa    19860
tcactcccag ctgtgtagcg aaggattgga gaaagggaaa atcagtaaca gcacaaaatt    19920
acaccacagt tttgggaacc tggaataacc tcagttcaag ggagtttcac agaagagggg    19980
cttggggaga gctagtgagc tggaggtgga ggccatgtct tgggatcagc tctgggctcc    20040
aggatgggat gccacggtaa gttctgaaac aagcttttat atgttaggct gttgaaattg    20100
agcctctgct gtccaagctc tcatttaagg tggtgacttt cttccctagg tgtaaaggac    20160
cagagcttca agactgtttt aggacaaacac tggtgctgat cgggtatgat ggggttggag    20220
attctggaaa ctggggatat ttgggagttg ggagagaggt ggttacctgg agagaagagg    20280
gaggctgtct tcattctggc cttttatgta tgcagtccac tatcactgga cacttgggac    20340
tcaagaatgc aggcttctgg acttcccttc ctaaaattaa ctttcagtag tctaagactg    20400
gtccagattt aggttggtcc cttcagtgct taaggatata tatgtgaatg ttaatttctt    20460
gccccaggtc agcatcatac cttcaacaca agtatagttg acatttgtaa ggaagatgca    20520
aacccaggat aatgttgggt ttctatatat cccatagcaa aacccatctg acaatggctt    20580
tgacagtgat agcaggattg gtagtgattt tcatgatgct gggcggcact tttctctact    20640
ggcgtgggcg ccggattcag aataaaaggg ctatgaggcg atacttggaa cggggtgagg    20700
tgagtactta gcttactttt gttttttctt ttcttttttt gcatgtcctg gaagtctctt    20760
tatagcttaa ttttgagtgg taccctgtgc acccaggggt cagtgatggg ataaatgtca    20820
ctcccctcct ctttccccag agatttgatc cctttcttca aggaagtagt gtggtcccct    20880
agaagaacac tggtcagaga aatgggaggc atgcattcta gtcctgattt tgccattaat    20940
ttgccacatg actttgaaga agttacttat cttctctgtg cctcggttta tgcatctata    21000
cagaggaaat aacatttgtc cttccaggat ggctgtaagg gtaaaggggg atgatgtatg    21060
tgaaagtgct ttggaaagca cagagcactg tataaaaggt actcaaggtg gtaatagtac    21120
taccaactct ccctagctgt cccccttccc actttgtgct cctccatcaa agggaaaacc    21180
caaccccttt gattcctgat ctcatgagca caaataactt cctcagttct cagggtctgt    21240
acctcaatat gcctataatc cattccagga ctaacggtgc ttcctcttcc tgcccttttca    21300 gctgtgctgc ttttggcatt cacctatgag gagcgggttg gagtgggaca tgggaatggc    21360
ctttcctgag taactccttc ccatttgctc ctcagagcat agagcctctg gaccccagtg    21420
agaaggctaa caaagtcttg gccagaatct tcaaagagac agagctaagg aagcttaaag    21480
tgcttggctc gggtgtcttt ggaactgtgc acaaagtgag tgacccatag gaattctgga    21540
gaggtgggga aggcatctag ggcaaagggg tgaaagattt ttgcataggga ttgacctagg    21600 gagaatgacc ttatgccaac tcctgcccca aacttcccag ggagtgtgga tccctgaggg    21660
tgaatcaatc aagattccag tctgcattaa agtcattgag acaagagtg gacggcagag    21720 ttttcaagct gtgacagatg taagtgaagg aaattctgta tgccgctagg agagaggaca    21780
atattagata caatcatgta gaagcagggt cctgtgcttc tcagcagcta ctatgttagc    21840
cagaatgttg ggggtggggg ggcctgggct ggctgtgcac atgctgagtg tatgtgaacc    21900
tgttggtttc ctagataata cctttttgtgt ctcttagcat atgctggcca ttggcagcct    21960
ggaccatgcc cacattgtaa ggctgctggg actatgccca gggtcatctc tgcagcttgt    22020
cactcaatat ttgcctctgg gttctctgct ggatcatgtg agacaacacc ggggggcact    22080
ggggccacag ctgctgctca actggggagt acaaattgcc aaggtgagag aagcctggag    22140
```

```
gaattctgtg ataagaactg cttgtctggg ggccagccag gaaaaagtga gaaggttgaa    22200
gttctgagag gtgaggtccc caaccccgg gctgcagact ggtaccagtc catggcctgt    22260
taggaaccag gccacagagc atgtgagcgg caggcaagcg agtgaagctt catctgtatt    22320
tacagtcagt ccccatcact tgcattaccg cccgagttcc gcctcctgtc agatcagggg    22380
cagcattaga ttctcttagg agcttgactt ctattgtgaa ctgtgcatgt gaaggatcta    22440
ggttgtgcac tccttatgag aatctaacta atgcctgatg atctgaggtg gaaaaatttc    22500
atcccaaaac caaccctccc cttcccctgg aaaaactgtc ttccacaaaa ccagtccctg    22560
gtgccaaaaa aggttgggga ccactgctga gaggtacctt caagatttgg gggaattcca    22620
gatctcagtg actgattccc ccaaccttaa gaatactttc ttccccctata cctacaggga    22680 atgtactacc ttgaggaaca tggtatggtg catagaaacc tggctgcccg aaacgtgcta    22740
ctcaagtcac ccagtcaggt tcaggtggca gattttggtg tggctgacct gctgcctcct    22800
gatgataagc agctgctata cagtgaggcc aaggtgagga gacacaaagg gtaaggaggc    22860
gggggtggag tgaagcatgg ggatagggag cagccagtgg tctcttccag aggcaagcag    22920
atgcttcatg gtaagttcaa ggagagaagg ctgcagatgc cagatatttt agttcagagg    22980
gcaacaaata aaataatgat caagaacttg ggactggccg ggcgcggtgg ctcacgcctg    23040
taatcccaac acttcgggag gccaaggcgg gtggatcaca aggtcaggag atcaagacca    23100
tcctggctag cacggtgaaa ccccgtctct actaaatata caaaaaaaaa aaaaattagc    23160
caggcgtggc ggcatgcatc tgtactccca gctactcggg aggctgaggc aggagaatgg    23220
cgtgaaccca ggaggcggag cttgcagtgg gccgagatcg caccactgca ctccagtctg    23280
ggcgacagag cgagactccg tctcaaaaaa aaaaaaaaa gaatttggga cttggaaatc    23340
ctaagaaaat ttgtggaaat aaacttgtga tacctctatc tttaatccgc agactccaat    23400
taagtggatg gcccttgaga gtatccactt tgggaaatac acacaccaga gtgatgtctg    23460
gagctatggt cagtgcatct ggatgccctc tctaccatca ctggcccag tttcaaattt    23520 acctttttgag accccctctt agaatctcta agcacttcag attttttgtgt tagatcaggt    23580 tctgccttcc cttcacttca tgcccatgtc tactattttg ccagtgacta gtccatgtct    23640
tcctgcaaca ggtgtgacag tttgggagtt gatgaccttc ggggcagagc cctatgcagg    23700
gctacgattg gctgaagtac cagacctgct agagaagggg gagcggttgg cacagcccca    23760
gatctgcaca attgatgtct acatggtgat ggtcaagtgt gagttacctg ctgagcccaa    23820 ccatttctc tttttttctt tttttttctt ttttttttt ttttgagaca gagtctcaca    23880
attgtcaccc aggctggagt gcaatggtgc aatcaatctt ggctcactac aacctccgcc    23940
tctcgggttc aagagattct cctgcttcag cctccggagt agctgggatt acaggcgccc    24000
gccacacctg gataactgtt acacttttag tagagatggg gtttcaccat gttggccagg    24060
ctggtctcaa actcctgacc tcaggtgatc cgcctgcctc agcttcccaa agtgctggga    24120
ttacaggtgt gagccatcat gctcggcctg actgcagcca ttttctgact tcctctgta    24180 ctcctcttat ggctctattc cttttttttt tatggagtct cgctctgttg cccatactgg    24240
agtgcagtag cgtgaccttg gctcaccgtg acctccacgt tccaggttta agttcttctg    24300
tctcagcctc ccagatagct gggactttag gcgtgcacca ccacgcccag ctaatttttt    24360
tttgtctttt tagtagagat gggggtttcac tatgttggcc aggctggtct caaagtcccg    24420
acctcaggtg atccacccgc cttggcctcc caaagtgctg ggattatagg tgtgagccac    24480
cgcgcccggc catggaatgt attctctttt atgtctctac ctcctacatc ttatctccag    24540
```

-continued

```
gttggatgat tgatgagaac attcgcccaa cctttaaaga actagccaat gagttcacca  24600
ggatggcccg agacccacca cggtatctgg tcataaaggt gagtagggag taggaggtgc  24660
taaggaaatt tagaaaaagg aggagttggc tggaaccagg attcccccta acaatcacct  24720
atcgatatag agagagagtg ggcctggaat agcccctggg ccagagcccc atggtctgac  24780
aaacaagaag ctagaggaag tagagctgga gccagaacta gacctagacc tagacttgga  24840
agcagaggag gacaacctgg caaccaccac actgggctcc gccctcagcc taccagttgg  24900
aacacttaat cggccacgtg gggtaagaca acttctaatt acccaacact ttgcaccctg  24960
agccctcaca aaccctacag atacccagat taactactca aaggccccca tggtgaatgt  25020
agatttctcc cttcatctta acctttcct tattttttca tcctagagcc agagccttt   25080 aagtccatca tctggataca tgcccatgaa ccagggtaat cttggggagt cttgccaggt  25140
aagttctgtt gctgagaggc tgggttttag gatcagattg atacgagtag tatggaagac  25200
attagaaacc tctgaggttt aatcagtgtc ctgcaaaaaa gaaggcagtg agggccgggc  25260
gagttggctc acacctgtaa tcccagcact ttgggaggcc agagagagtg gatcacctga  25320
ggttaggagt ttgagaccag cctggccaac atggtgaaac cccgtctcta cccaaaatac  25380
aaaaattagc tgggtgtggt ggtgcacacc tgtaatcaca gctactcagg aggctgagac  25440
aggagaatcg cttgaacccg ggaggcagag gttgcagtga gctgagattg taccactgca  25500
ctccagcctg ggtgacagag caagaccctg tctcttaaaa aaaaaaaaa aaggccaggt  25560 gcggtggctc acgcctgtaa tcctagcact ttgggaggcc gaggtgggcg gatcatgagg  25620
tcaggagttc gagaccagcc tgaccaacat ggcaaaaccc tgtctgtact aaaaatacaa  25680
aaactagctg cacatgatgg caggtgcctg taatcccagc tactcgggag gctgaggcag  25740
gagaatcact tgaacaggga agcagaggct gcagtgagcc aagataatgc cactgcactc  25800
cagcctgggc gacaagaaca agactccacc tcaaaaaaaa aaaaaaaaaa aaaaaaggc  25860 agtgaacaac ccaatatcct tctaaacaaa tctctcttct ttcctcatca tgtaaatttc  25920
cttgcattat tttctgttta ttttcttcct taggagtctg cagtttctgg gagcagtgaa  25980
cggtgccccc gtccagtctc tctacaccca atgccacggg gatgcctggc atcagagtca  26040 tcagagggc atgtaacagg ctctgaggct gagctccagg agaaagtgtc aatgtgtagg  26100
agccggagca ggagccggag cccacggcca cgcggagata gcgcctacca ttcccagcgc  26160
cacagtctgc tgactcctgt taccccactc tccccacccg ggttagagga agaggatgtc  26220
aacggttatg tcatgccaga tacacacctc aaaggtgcct gactcttcct agggcttttcc  26280 tcaattttc ctcgaattct ttccccgggc tcctcttttt tcttctctga tcatatgcct  26340
ctctgtccta ttaatttttt caaactttcc cctaccctca tgaagttctt cacataccta  26400
gcctttcttc tcaaccccca ggtactccct cctcccggga aggcacccctt tcttcagtgg  26460 gtctcagttc tgtcctgggt actgaagaag aagatgaaga tgaggagtat gaatacatga  26520
accggaggag aaggcacagt ccacctcatc cccctaggcc aagttccctt gaggagctgg  26580
gttatgagta catggatgtg gggtcagacc tcagtgcctc tctgggcagc acacagagtt  26640
gcccactcca ccctgtaccc atcatgccca ctgcaggcac aactccagat gaagactatg  26700
aatatatgaa tcggcaacga gatggaggtg gtcctggggg tgattatgca gccatgggggg  26760 cctgcccagc atctgagcaa gggtatgaag agatgagagc ttttcagggg cctgagacatc  26820 aggccccca tgtccattat gcccgcctaa aaactctacg tagcttagag gctacagact  26880
```

```
ctgcctttga taaccctgat tactggcata gcaggctttt ccccaaggct aatgcccaga    26940
gaacgtaact cctgctccct gtggcactca gggagcattt aatggcagct agtgccttta    27000
gagggtaccg tcttctccct attccctctc tctcccaggt cccagcccct tttccccagt    27060
cccagacaat tccattcaat ctttggaggc ttttaaacat tttgacacaa aattcttatg    27120
gtatgtagcc agctgtgcac tttcttctct ttcccaaccc caggaaaggt tttccttatt    27180
ttgtgtgctt tcccagtccc attcctcagc ttcttcacag gcactcctgg agatatgaag    27240
gattactctc catatccctt cctctcaggc tcttgactac ttggaactag gctcttatgt    27300
gtgcctttgt ttcccatcag actgtcaaga agaggaaagg gaggaaacct agcagaggaa    27360
agtgtaattt tggtttatga ctcttaaccc cctagaaaga cagaagctta aaatctgtga    27420
agaaagaggt taggagtaga tattgattac tatcataatt cagcacttaa ctatgagcca    27480
ggcatcatac taaacttcac ctacattatc tcacttagtc ctttatcatc cttaaaacaa    27540
ttctgtgaca tacatattat ctcattttac acaaagggaa gtcgggcatg gtggctcatg    27600
cctgtaatct cagcactttg ggaggctgag gcagaaggat tacctgaggc aaggagtttg    27660
agaccagctt agccaacata gtaagacccc catctcttta aaaaaaaaa aaaaaaaaaa    27720 aaaaaaactt tagaactggg tgcagtggct catgcctgta atcccagcca gcactttggg    27780
aggctgagat gggaagatca cttgagccca gaattagaga taagcctatg gaaacatagc    27840
aagacactgt ctctacaggg gaaaaaaaaa aagaaactg agccttaaag agatgaaata    27900
aattaagcag tagatccagg atgcaaaatc ctcccaattc ctgtgcatgt gctcttattg    27960
taaggtgcca agaaaaactg atttaagtta cagcccttgt ttaaggggca ctgtttcttg    28020 ttttttgcact gaatcaagtc taaccccaac agccacatcc tcctatacct agacatctca    28080
tctcaggaag tggtggtggg ggtagtcaga aggaaaaata actggacatc tttgtgtaaa    28140
ccataatcca catgtgccgt aaatgatctt cactccttat ccgagggcaa attcacaagg    28200
atccccaaga tccacttttta gaagccattc tcatccagca gtgagaagct tccaggtagg    28260
acagaaaaaa gatccagctt cagctgcaca cctctgtccc cttggatggg gaactaaggg    28320
aaaacgtctg ttgtatcact gaagtttttt gttttgtttt tatacgtgtc tgaataaaaa    28380
tgccaaagtt ttttttcagc ttcctgtctg tcaaatgaag acatttcgta tgttagataa    28440
gagatctgct cctcagcagt ggatactcac ctttctgtgt tctgacagtg ctactctgtc    28500
ccatgcagct ttctctagtc ctactattac ttctatttct ttagaacaac catagcgcat    28560
agtccttttc attaagggtt ttagtaggaa tctacaaggc aaccaattgg gaataacaaa    28620
aagaacctac gtgctttagg acttataaaa agccctataa gccctccttc agaggccaaa    28680
cactgaaacc tccagatgct tctgaattca ttatcttaga aaagtcatca aatctttta    28740 tttttttcacg gtaagaactc tcaacaaaca tgtctttctg aacacttccc ttaggtgctc    28800
catccaggtg cctgttattg gaacaataaa gtcatgttac ttcattagga gtccggcctc    28860
tagattgcga ggccttaaa tggatgatcc ctccggtgtc tggctgccca gttagccccc    28920
gttaccagca cccttggtct tcttccacct gtctgcccct ccctgttctc ccagcttcgg    28980
aggacgactg gaccggctgg gcgggtttcg ccagccgacc cagggatccg aagaagggcg    29040
cacccagcct ccccgaccta ggtgtagaca ctgcccaccc gctgcggctc cactctactc    29100 caccctgcc cgctcgactt taaacctatt tcccgccgt agctccgccc ctctccctc    29160 agcccgcccc tctctgttac tggctctcgc tcagcgttct cggtggaagt ggtttttccg    29220
ggagagacca cgcttcccct caagctcccc aacggctccg ccttcccgcc ggagcctgac    29280
```

```
cctteccaga gtgeceggeg attecggegt gegaggecet tggagggeaa ggceccaggg    29340 cctggettag gagcgcgaga ggcaggetgg gaattgtagt tcgaaggeee tcgagagegg    29400 ctagagtctg gcggccgaga ggactagttg tcccagcgtg ccctgcgect cagcccgcgc    29460 gctcgcaget tctcgctctc gcctgcctgc ccgctccctt gcttgctcgc gctttcgctc    29520
gccctctcct cgaggatcga ggggactctg accacagcct gtggctggga agggagacag    29580
aggcggcggc ggctcagggg aaacgagget gcagtggtgg tagtaggaag atgtcgggcg    29640
aggacgagca acaggagcaa actatcgctg aggacctggt cgtgaccaag tataagatgg    29700
ggggcgacat cgccaacagt gagtgcggcc tcggggtcg gggaatcaag gctgataggg     29760
aaaggtaaca ggctggcccg aaggggctg gagcggaggg gtcatgcgga ctgagctact      29820
gaggggcccg caccggtccg ctgggcacgg cgtggtggga agacccggtg tcgcgcctgg    29880
gacctgagcg ggcaggccca ggctgaagtc tatggaggtg cgggtcggcg accaggatga    29940
gcgcagagag gggaccctgg caggctccga cccgaggccg tttgttagga ggcaagacgt    30000
gttttctctt gttcctatcc ttcattcccg attattgctt cctctgattc tggcagcggc    30060
gaggccacct cgaaaaggaa gcgcccagct attggcgaca gaagtgcccc tctgtttttg    30120
tagcgtctcc ggggcgtcag gagccaagcc ggcacgtgtt gctgggtccc attgcggatg    30180
gctggccccc ttcttactcc gctagtgtcc ctgacaccag cttccccacc accagct       30237

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 5

Asn Leu Arg Val Val Arg Gly Thr Gln Val Tyr
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 6

Asp Lys Leu Cys His Met Asp Thr Ile Asp Trp Arg Asp Ile Val
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 7

Pro Cys His Glu Val Cys Lys
1               5

<210> SEQ ID NO 8
<211> LENGTH: 15
<212> TYPE: PRT
```

<213> ORGANISM: Artificial Sequence
<220> FEATURE:
<223> OTHER INFORMATION: Synthetic peptide derived from HER3 protein sequence

<400> SEQUENCE: 8

Ile Cys Ala Pro Gln Cys Asn Gly His Cys Phe Gly Pro Asn Pro
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide derived from HER3 protein sequence

<400> SEQUENCE: 9

Asn Gly Asp Pro Trp His Lys
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide derived from HER3 protein sequence

<400> SEQUENCE: 10

Asp Pro Leu Cys Ser Ser Gly Gly Cys Trp Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide derived from HER3 protein sequence

<400> SEQUENCE: 11

Cys Pro His Gly Val Leu Gly Ala Lys Gly Pro
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide derived from HER3 protein sequence

<400> SEQUENCE: 12

Ile Ala Gly Leu Val Val Ile Phe Met Met Leu Gly Gly Thr Phe
1               5                   10                  15

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide derived from HER3 protein sequence

<400> SEQUENCE: 13

Leu Glu Arg Gly Glu Ser Ile Glu Pro Leu Asp
1               5                   10

```
<210> SEQ ID NO 14
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 14

Gln Leu Leu Tyr Ser Glu Ala Lys Thr Pro Ile
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 15

Glu Ser Ile His Phe Gly Lys Tyr Thr His Gln Ser Asp Val Trp
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 16

Val Trp Glu Leu Met Thr Phe Gly Ala Glu Pro Tyr Ala Gly Leu
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 17

Glu Ser Gly Pro Gly Ile Ala Pro
1               5

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 18

Thr Leu Asn Arg Pro Arg Gly Ser Gln Ser Leu Leu Ser Pro Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence
```

<400> SEQUENCE: 19

Glu Ala Glu Leu Gln Glu Lys Val Ser Met Cys Arg Ser Arg Ser
1               5                   10                  15

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 20

Glu Glu Asp Val Asn Gly Tyr Val Met Pro Asp
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 21

Met Pro Thr Ala Gly Thr Thr
1               5

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 22

Asp Gly Gly Gly Pro Gly Gly Asp Tyr Ala Ala Met
1               5                   10

<210> SEQ ID NO 23
<211> LENGTH: 35
<212> TYPE: DNA
<213> ORGANISM: Artificial Sequence
<220> FEATURE:
<223> OTHER INFORMATION: Synthetic primer: hHER3-F

<400> SEQUENCE: 23
cagggcggcc gcaccatgag ggcgaacgac gctct                          35

<210> SEQ ID NO 24
<211> LENGTH: 37
<212> TYPE: DNA
<213> ORGANISM: Artificial Sequence
<220> FEATURE:
<223> OTHER INFORMATION: Synthetic primer: hHER3-ECDTM-R

<400> SEQUENCE: 24
acaagcggcc gcagttaaaa agtgccgccc agcatca                        37

<210> SEQ ID NO 25
<211> LENGTH: 39
<212> TYPE: DNA
<213> ORGANISM: Artificial Sequence
<220> FEATURE:
<223> OTHER INFORMATION: Synthetic primer: hHER3-ECD-R

```
<400> SEQUENCE: 25
acaagcggcc gcatttatgt cagatgggtt ttgccgatc                              39

<210> SEQ ID NO 26
<211> LENGTH: 33
<212> TYPE: DNA
<213> ORGANISM: Artificial Sequence
<220> FEATURE:
<223> OTHER INFORMATION: Synthetic primer: hHER3-ECDC1C2-R

<400> SEQUENCE: 26
acaagcggcc gcattgtcag atgggttttg ccg                                    33
```

VACCINES AGAINST ANTIGENS INVOLVED IN THERAPY RESISTANCE AND METHODS OF USING SAME

CROSS-REFERENCE TO RELATED APPLICATIONS

This patent application is a national stage filing under 35 U.S.C. 371 of International Application No. PCT/US2013/022396, filed Jan. 21,2013, which claims the benefit of priority of U.S. Provisional Patent Application No. 61/588,449, filed Jan.19, 2012, both of which are incorporated herein by reference in their entirety.

STATEMENT REGARDING FEDERALLY SPONSORED RESEARCH

This invention was made with United States government support awarded by the National Cancer Institute grant numbers P50 CA89496-01, P50 CA068438 and R01 CA95447 and by Department of Defense grant number BC050221. The United States has certain rights in this invention.

This application was filed electronically via EFS -Web and includes an electronically submitted Sequence Listing in .txt format. The .txt file contains a sequence listing entitled "2013-01-21_5667-00104_Sequence_Listing_as_Filed" created on Jan. 21, 2013 and is 64.7kilobytes in size. The Sequence Listing contained in this .txt file is part of the specification and is hereby incorporated by reference herein in its entirety.

INTRODUCTION

This application relates to a cancer vaccine, specifically a vaccine against antigens that are expressed in response to resistance to therapeutic intervention to cancer (or pre-cancers), with a proof of principle antigen, HER3, as an example. Methods of using the vaccines and methods of developing vaccines capable of blocking the development of resistance to cancer therapies are also provided.

Cancer vaccines target antigens expressed by tumors, but application of these vaccines has not been as effective as once hoped due to induction of immune tolerance by chronic overexpression of the targeted protein in the absence of co-stimulatory molecules and the induction of an immuno-modulatory environment. Preventative cancer vaccines may be more promising, but cancers are highly variable, with multiple genetic changes, but few truly universal changes. Thus, it is difficult to predict what antigens will be overexpressed on any specific cancer or whether an individual should be vaccinated and if so, with what antigens. In contrast, a strategy is proposed here in which vaccination against the antigen(s) that will predictably be overexpressed in response to a therapy, but prior to that antigen's overexpression by the cancer cells is used to induce a robust anti-cancer immune response.

SUMMARY

Provided herein is a mechanism of revolutionizing cancer therapy or prevention by preventing the development of resistance to cancer therapeutic or cancer prevention agents by identifying which antigens are likely to be expressed in a cancer or precancer in response to treatment with a cancer therapeutic or prevention agent and thus which antigens may be targeted with a vaccine in patients. Also provided is a vaccine targeting a specific antigen involved in a resistance mechanism, namely HER3, and methods of using the vaccine. In one aspect, the vaccine includes a polynucleotide encoding a HER3 polypeptide. For example, a HER3 polypeptide of SEQ ID NO: 1 or 2 may be included in a vaccine.

In another aspect, methods of treating a cancer or precancer or reducing the likelihood of the cancer or precancer to develop resistance to a cancer therapeutic or prevention agent by administering the vaccine provided herein to a subject with cancer or precancer are provided. The vaccine may be administered before, concurrently with or after administration of the cancer therapeutic or prevention agent.

In yet another aspect, methods of reducing the likelihood of a cancer or precancer developing resistance to a cancer therapeutic or prevention agent by administering the cancer therapeutic or prevention agent and a vaccine to the subject are provided. The vaccine includes a polynucleotide encoding a polypeptide whose expression or activation correlates with development of resistance of the cancer or precancer to the cancer therapeutic or prevention agent. Co-administration of the cancer therapeutic or prevention agent and the vaccine inhibits the generation of resistance to the cancer therapeutic or prevention agent and increases the therapeutic potential of the cancer therapeutic agent and the prevention potential of the cancer prevention agent.

BRIEF DESCRIPTION OF THE DRAWINGS

FIG. 1 is a set of figures showing HER3 specific T cell and B cell responses to Ad-HER3 in vivo. FIG. 1D shows the results of epitope mapping of HER3-VIA using spotted 15mer peptide arrays and revealed recognition of 18 different epitopes.

FIG. 2 is a set of figures showing that HER3-VIA mediate multiple mechanisms of action on human breast tumor cell lines in vitro. FIG. 2B is a graph showing that HER-3 VIA mediate antiproliferative activity against HER3-expressing (BT474, T47D, MDA-MB-468, BT474M1) human breast cancer cell lines but not against the HER3-negative cell line (MDA-MB-231) in a 72 hour assay. The antiproliferative effect implied receptor modulation

FIG. 3 is a set of figures showing the in vive effects of HER3-VIA on BT474M1 human breast tumor xenografts. FIG. 3D is a set of photographs of Western blot analysis of excised tumors for expression of the indicated proteins.

FIG. 4 is a set of figures showing the in vivo effects of HER3-VIA in lapatinib-refractory rBT474 SCID tumor xenografts.

DETAILED DESCRIPTION

Figure 1A:
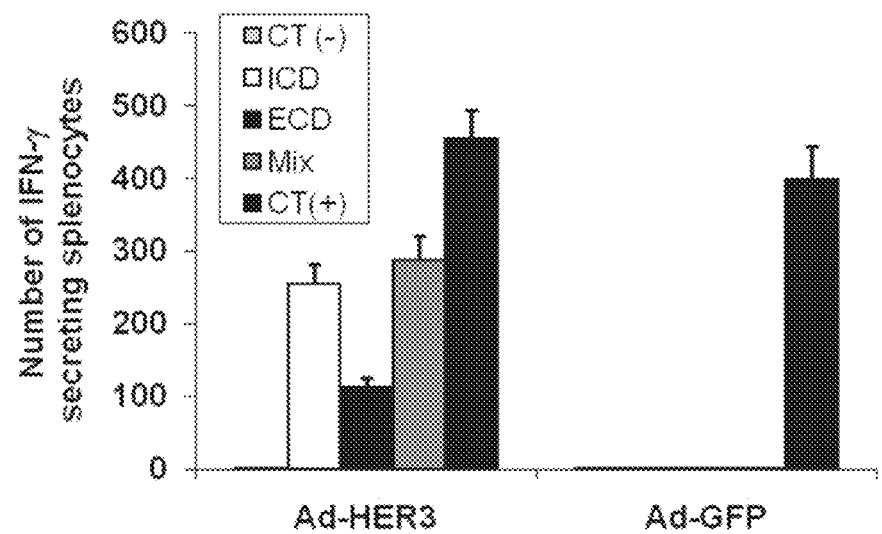
FIG. 1A is a graph showing the number of IFN-γ secreting splenocytes by ELISPOT after 6-8 week old BALB/c mice were immunized once with $2.6 \times 10^{10}$ Ad-HER3 or Ad-GFP via bilateral subcutaneous footpad injections. Two weeks following the vaccination mice were euthanized and splenocytes collected for analysis in an Interferon-gamma ELISPOT assay. Splenocytes from Ad-HER3 vaccinated and not or Ad-GFP vaccinated (control) mice recognized HER3 intracellular domain (ICD) and extracellular domain (ECD) peptide libraries and the mixture of both libraries (Mix) in interferon-gamma ELISPOT assays. The mean from 5 mice per group is shown with error bars denoting standard deviation. CT−; splenocytes alone. CT+; Splenocytes plus PMA (50 ng/mL) and lonomycin (I ng/mL) as a control for the assay.

As a novel alternative to vaccines targeting well established tumor antigens, we hypothesized that the antigen-specific immune non-responsiveness to conventional tumor-associated antigens may be avoided by targeting tumor antigens that are induced after exposure to a cancer therapeutic or prevention agent as a mechanism of developing therapeutic resistance. Although there may be many potential antigens overexpressed in response to a cancer therapeutic or prevention agent, those antigens that are likely critical components of specific therapeutic resistance mechanisms would be attractive targets, as immunologic ablation of clones expressing such antigens should eliminate the clinical recurrence of therapy resistant tumor cells. One such antigen thought to be essential to therapeutic resistance is a member of the HER family of receptor tyrosine kinases (RTKs), and to endocrine therapies, HER3.

HER3, although lacking catalytic kinase activity, is thought to function as a signaling substrate for other HER proteins with which it heterodimerizes. Although not transforming by itself, HER3 has tumor promoting functions in some cancers, including a role as a co-receptor for amplified HER2 with which it is synergistically co-transforming and rate-limiting for transformed growth. Treatment of HER2-amplified breast cancers with HER2-targeting tyrosine kinase inhibitors (TKis) leads to an increase in HER3 expression and downstream signaling that results in therapeutic resistance.

The pivotal role of HER3 as a hub for HER family signaling has made it an attractive therapeutic target, but its' lack of kinase activity prevents small molecule HER3 specific TKIs from being generated. Nonetheless, HER3 may be targeted with antibodies which have diverse functional consequences depending on their binding site. For example, the anti-HER2 monoclonal antibody pertuzumab disrupts neuregulin-induced HER2-HER3 dimerization and signaling; however, it is less effective at disrupting the elevated basal state of ligand-independent HER2-HER3 interaction and signaling in HER2-overexpressing tumor cells. Other HER3-specific antibodies under development bind to, and cause internalization of, HER3, inhibiting downstream signaling. As an alternative to monoclonal antibodies, we have recently demonstrated that polyclonal antibodies induced by vaccination against receptors such as HER2 can mediate profound receptor internalization and degradation, providing a therapeutic effect in vitro and in rivo (Ren et al., Breast cancer Research 2012 14: R89).

Therefore, we generated a recombinant adenoviral vector expressing human HER3 (Ad-HER3) and demonstrated that it elicited HER3 specific B and T cell immune responses as shown in the Examples. Furthermore, we demonstrated that HER3 specific antibodies recognized multiple HER3 epitopes, bound to tumor membrane expressed HER3, mediated complement dependent lysis and altered downstream signaling mediated by receptor heterodimers involving HER3. In addition, we found that HER3 specific polyclonal antisera had specific activity in mediating HER3 internalization and degradation. Finally, we demonstrated that HER3 specific polyclonal antisera was well tolerated when transferred to tumor bearing animals, yet retarded tumor growth in vivo, including retarding the growth of HER2 therapy-resistant tumors. These data suggest that Ad-HER3 is an effective vaccine which should be tested for therapeutic efficacy in clinical trials targeting cancers that overexpress HER3 in response to a targeted therapy. The general application of this vaccination strategy can be applied to other antigens expressed in HER therapy resistant tumors, as well as antigens induced by other resistance mechanisms, and represents a new conceptual framework for cancer immunotherapy.

As described in the appended examples, generation of resistance to cancer therapeutic or prevention agents is a common problem in the treatment of cancer or precancer and in several cases the mechanism of resistance to the therapeutic agent is known. Resistance is often the result of changes in gene expression (over-expression or blocked expression of a protein), change in the gene by mutation, or altered sequences by altered splicing or translocation or altered activation of a protein in the cells (over-activation or blocked activation of a protein).

In those cases where over-expression or over-activation of a protein, or a new sequence in the protein is responsible for increasing the resistance of the cancer or precancer cells to the therapeutic or prevention agent, we report a method for reducing the likelihood that the cancer or precancer will develop resistance to the cancer therapeutic or prevention agent. As used herein, resistance to a cancer therapeutic or prevention agent indicates that the cancer therapeutic or prevention agent is not as effective at inhibiting the growth of, or killing, cancer or precancer cells in response to the cancer therapeutic or prevention agent. The method may even block the development of resistance to the cancer therapeutic or prevention agent or may reverse resistance to the cancer therapeutic or prevention agent after it has developed. The methods include administering the cancer therapeutic or prevention agent and administering a vaccine to the subject in need of treatment for a cancer. The vaccine comprises a polynucleotide encoding a polypeptide whose expression or activation is correlated with or results in development of resistance of the cancer or precancer to the cancer therapeutic or prevention agent.

The vaccine may be administered before, during or after treatment with the cancer therapeutic or prevention agent or may be administered simultaneously with the cancer therapeutic or prevention agent. The administration of the vaccine and the cancer therapeutic or prevention agent to the subject reduces the likelihood that the subject's cancer or precancer will develop resistance to the therapeutic or prevention agent as compared to a control subject with a similar cancer or precancer not administered the vaccine or as compared to the general likelihood of a population of subjects having the cancer or precancer. In some embodiments, the cancer or precancer in individuals administered both the vaccine and the therapeutic or prevention agent does not develop resistance to the cancer therapeutic or prevention agent and is treated. Alternatively, the growth of the cancer or precancer may be inhibited or the growth rate reduced. The administration of the vaccine and cancer therapeutic or prevention agent may also reverse resistance to the cancer therapeutic or prevention agent if the cancer or precancer is already resistant to the cancer therapeutic or prevention agent. In some embodiments, administration of the vaccine is sufficient to treat the cancer or inhibit the growth or kill the cancer. In other embodiments, the vaccine must be administered in conjunction with the cancer therapeutic or prevention agent or prior to development of resistance to the cancer therapeutic or prevention agent by the cancer.

The vaccine may include a polynucleotide encoding a HER3 polypeptide. The mature HER3 protein sequence is provided in SEQ ID NO: 1 and the complete HER3 protein precursor sequence is provided in SEQ ID NO: 2. Polynucleotide sequences for HER3 are provided in SEQ ID NO:3 (mRNA) and SEQ ID NO: 4 (DNA). The vaccine may comprise full-length HER3 or portions thereof. For example, the vaccine may comprise only the extracellular domain or the extracellular domain plus the transmembrane domain or other portions of the HER3 polypeptide. Suitably the vaccine is capable of eliciting an immune response to HER3 in a subject administered the vaccine. The immune response may be a B cell or T cell response. Suitably the immune response includes an antibody response directed to HER3. The immune response may be a polyclonal antibody response in which multiple epitopes of HER3 are recognized by antibodies.

As reported in the examples, in a mouse model a HER3 vaccine was able to generate a robust polyclonal antibody response to HER3 and several epitopes were identified. See FIG. 1D. The epitopes identified in FIG. 1D include the polypeptides identified in SEQ ID NOs: 5-22, which represents portions of SEQ ID NO:2. It is expected that some of these epitopes may be immunogenic in humans as well. Those of skill in the art will appreciate that a vaccine including polynucleotides encoding only portions of full-length HER3, i.e. antigenic epitopes, may be used in the vaccines described herein.

The vaccine may include a vaccine vector. The vaccine vector may be a bacterial, yeast, viral or liposomal vaccine vector. The vaccine may be a DNA vaccine as well and not include a vaccine vector. The vaccine vector may be an adenovirus or adeno-associated virus. In the Examples an adenovirus was used as the vaccine vector. The vaccine vector may contain the HER3 polynucleotide or portions thereof. The vaccine vector may contain the HER3 polypeptide or portions thereof. The vaccine vector may express the HER3 polypeptide or portions thereof. HER3 polypeptide or portions thereof may be expressed on the surface or interior of the vaccine vector. HER3 polynucleotide or portions thereof may be carried within the vaccine vector and the HER3 polypeptide or portions thereof may be expressed only after vaccination. HER3 polypeptides or portions thereof may be expressed as a fusion protein or in conjunction with adjuvants or other immunostimulatory molecules to further enhance the immune response to the polypeptide.

Methods of treating a cancer or precancer, or of reducing the likelihood of the cancer or precancer developing resistance to a cancer therapeutic or prevention agent, are also provided. The methods include administering the vaccine as described above to a subject having cancer or precancer. The subject may be any mammal, suitably a human, domesticated animal such as a dog or cat, or a mouse or rat. A cancer therapeutic or prevention agent may be administered concurrently with, before or after administration of the vaccine.

The cancer therapeutic or prevention agents may be any agent capable of treating the cancer or inhibiting growth of cancer cells. Suitable agents include those which target HER2, HER1/EGFR, estrogen receptor or IGF1R. The therapeutic agent may be trastuzumab, lapatinib, pertuzumab or another HER2 targeting therapeutic agent or it may be an EGFR targeting therapeutic agent such as cetuximab or erlotanib, or it may be an antiestrogen, or an agent that prevents estrogen synthesis such as an aromatase inhibitor. In particular, the Examples demonstrate that a HER3 vaccine can treat a HER2 positive cancer when used in combination with a therapeutic agent targeting HER2. Cancer cells often develop resistance to HER2 targeting therapeutic agents. Addition of vaccination with a HER3 vaccine or passively transferred polyclonal antibodies specific for HER3 resulted in blocking resistance, inhibited cancer cell growth and resulted in treatment of the cancer.

Suitably the vaccinated subject develops an immune response to HER3 in response to administration of the vaccine. The immune response may be an antibody or T cell immune response. For example the immune response may include antibody-dependent cellular cytotoxicity, polyclonal antibody response, complement dependent cellular cytotoxicity, cellular cytotoxicity, disruption of ligand binding, disruption of dimerization, mimicking ligand binding causing internalization of HER3, or degradation of HER3. The immune response may comprise an antibody response directed to at least one of SEQ ID NOs: 5-22. As shown in the Examples, transfer of HER3 specific antibodies was sufficient to treat the cancer and inhibit the development of resistance to the therapeutic agent.

Reduction of the development of resistance can be measured in several ways. The resistance of the vaccinated subject may be compared to a similar subject that was not vaccinated as in the Examples. Alternatively, the reduction may be measured based on statistics generated regarding the likelihood of an individual being treated with the therapeutic agent to develop resistance versus that of individuals treated with the therapeutic agent and vaccinated with HER3. The reduction in the likelihood of resistance of the cancer may also be measured by measuring the level of HIER3 expression on the surface of cancer cells. HER3 expression is reduced on cancer cells after effective administration of the vaccine. The effectiveness of the vaccine in treating the cancer or reducing the likelihood of resistance can be measured by tracking the growth of the tumor or the growth rate of the tumor or cancer cells. A decrease in tumor size or in the rate of tumor growth is indicative of treatment of the cancer.

The cancer may be selected from any cancer capable of developing resistance to a therapeutic agent by increasing expression or activation of a protein by the cancer cells. In particular the cancer may be any cancer capable of developing resistance to a therapeutic agent which targets a HER family tyrosine kinase, suitably HER2 or EGFR or the estrogen receptor, suitably anti-estrogens. The cancer may develop resistance by increasing the expression of HER3, which although not a kinase, will dimerize with another HER family kinase and allow for signaling to occur. Suitably the cancers are selected from breast, prostate, lung, ovarian, colon, rectal, pancreas, bladder, head and neck or liver cancers or precancers. The resistance may be due to a single or multiple changes, and the vaccine can target one or more of these changes, and/or include multiple antigens likely found in resistance cells, but not necessarily in all resistance cells.

Treating cancer includes, but is not limited to, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

Co-administration, or administration of more than one composition (i.e. a vaccine and a therapeutic agent) to a subject, indicates that the compositions may be administered in any order, at the same time or as part of a unitary composition. The two compositions may be administered such that one is administered before the other with a difference in administration time of 1 hour. 2 hours, 4 hours, 8 hours, 12 hours, 16 hours, 20 hours, 1 day, 2 days, 4 days, 7 days, 2 weeks, 4 weeks or more.

An effective amount or a therapeutically effective amount as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions (i.e. the vaccines and the therapeutic agents) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or transmucosal absorption. Thus the compositions may be formulated as an ingestable, injectable, topical or suppository formulation. The compositions may also be delivered with in a liposomal or time-release vehicle. Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compositions will reduce the growth of the cancer at least 10%, 20%, 30%, 40%, 50%, 60%, 70%, 80%, 90%, 100% or more as compared to no treatment or treatment with only the therapeutic agent. It is specifically contemplated that pharmaceutical preparations and compositions may palliate, block further growth or alleviate symptoms associated with the cancer without providing a cure, or, in some embodiments, may be used to cure the cancer and rid the subject of the disease.

The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The vaccine vector may be administered one time or more than one time to the subject to effectively boost the immune response against HER3. If the vaccine is provided as a vaccine vector, the vaccine vector may be administered based on the number of particles delivered to the subject (i.e. plaque forming units or colony forming units). The subject may be administered $10^{12}$, $10^{11}$, $10^{10}$, $10^9$, $10^8$, $10^7$ or $10^6$ particles.

The examples provided herein are meant only to be illustrative and are not meant as limitations on the scope of the invention or of the appended claims. All references cited herein are hereby incorporated by reference in their entireties.

EXAMPLES

Materials and Methods
Cell Lines and Cell Culture Reagents.

The human breast cancer cell lines BT474, MCF-7, MDA-MB-231, MDA-MB-468, SKBR3, and T47D were obtained from the ATCC and grown in recommended media. The BT474M1 human breast tumor cell line was a gift from Dr. Mien-Chic Hung at The University of Texas M. D. Anderson Cancer Center and was grown in DMEM/F12 with 10% FBS. Laptinib-resistant BT474 (rBT474) were generated as previously described. Xia et al. A model of acquired autoresistance to a potent ErbB2 tyrosine kinase inhibitor and a therapeutic strategy to prevent its onset in breast cancer. Proc Natl Acad Sci USA 2006; 103:7795-800. Trastuzumab (Herceptin™, Genentech, San Francisco, Calif.) was purchased from the Duke Pharmacy.
Adenovirus Vector Preparation.

The human HER3 cDNA was excised from a pCMVSport6-HER3-HsIMAGE6147464 plasmid (eDNA clone MGC:88033/IMAGE:6147464) from the ATCC (Manassas, Va.), and construction of first-generation [E1-, E3-] Ad vectors containing human full length HER3 under control of human CMV promoter/enhancer elements was performed using the pAdEasy system (Agilent technologies, Santa Clara, Calif.) as previously described. Morse et al. Synergism from combined immunologic and pharmacologic inhibition of HER2 in vivo. Int J Cancer 2010; 126:2893-903; Amalfitano et al. Production and characterization of improved adenovirus vectors with the E1, E2b, and E3 genes deleted. J Virol 1998; 72:926-33; Hartman et al. An adenoviral vaccine encoding full-length inactivated human Her2 exhibits potent immunogenicty and enhanced therapeutic efficacy without oncogenicity. Clin Cancer Res 2010; 16:1466-77; and He et al. A simplified system for generating recombinant adenoviruses. Proc Natl Acad Sci USA 1998; 95; 2509-14.
Mice.

BALB/c and NOD.CB 17-Prkdc$^{scid}$/J mice were purchased from Jackson Labs (Bar Harbor, Me.). All work was conducted in accordance with Duke IACUC-approved protocols. Induction of VIA: BALB/c mice were vaccinated on day 0 and day 14 via footpad injection with Ad-GFP, or Ad-HER3 vectors ($2.6 \times 10^{10}$ particles/mouse). Fourteen days after the second vaccination, mice were euthanized and sera were collected and stored at −80° C.
MTT Assay to Detect Cell Proliferation.

The effect of VIA-HER3 on the proliferation of human breast cancer cell lines was measured as previously described. Morse et al. Synergism from combined immunologic and pharmacologic inhibition of HER2 in vivo. Int J Cancer 2010; 126:2893-903. Briefly, 5000 cells per well in a 96-well plate were cultured with HER3-VIA (1:33 dilution) or control serum GFP-VIA (1:33 dilution) or Trastuzumab 20 µg/ml for 3 days and proliferation was assessed by MTT assay.
Western Blotting to Analyze Pathway Inhibition.

Tumors were isolated from euthanized mice and immediately flash frozen. Tissue extracts were prepared by homogenization in RIPA buffer as previously described by Morse et al. 2010. Equal amounts of proteins (50 ug) were resolved by 4-15% gradient SDS PAGE After transfer membranes were probed with specific antibodies recognizing target proteins: pTyr (Sigma), ErbB2, ErbB3, Akt, pAkt473, Erk 1/2, pErk1/2, (Cell Signaling, Beverly, Mass.) survivin, and actin (Sigma, St. Louis, Mo.), 4EBP-1, p4EBP-1, s6, ps6 (Santa Cruz Biotech., Santa Cruz, Calif.) and IRDye 800 conjugated anti-rabbit or mouse IgG or Alexa Fluor 680 anti-rabbit IgG and were visualized using the Odyssey Infrared Imaging System (LI-COR, Lincoln, Nebr.).
ELISPOT Analysis.

IFN-gamma ELISPOT assays (Mabtech, Cincinnati, Ohio) performed as previously described by Morse et al, 2010. HER3 peptide mix (1 mcg/mL was used; Jerini Peptide Technologies, Berlin, Germany), HIVgag peptide mix (BD Bioscience), or a mixture of PMA (50 ng/mL) and Ionomycin (1 ng/mL) were used. Six replicate wells for each condition were scored using the KS ELISPOT Reader with the KS ELISPOT 4.9 Software (Carl Zeiss, Miinchen-Hallbergmoos, Germany), reporting responses as the mean of the replicate 6 wells.
Analysis of Anti-HER3 Antibody Binding by Flow Cytometry.

We have adapted a methodology reported by Piechocki et al. to measure anti-HER3 vaccine induced antibodies in vaccinated mouse serum by flow cytometry. Hartman et al. An adenoviral vaccine encoding full-length inactivated human Her2 exhibits potent immunogenicty and enhanced therapeutic efficacy without oncogenicity. Clin Cancer Res 2010; 16:1466-77 and Piechocki et al. Quantitative measurement of anti-ErbB-2 antibody by flow cytometry and ELISA. J Immunol Methods 2002; 259:33-42. Briefly, $3 \times 10^5$ human breast cancer cells were incubated with diluted (1:100 to 1:51,200) mouse serum antibodies (HER3-VIA or GFP-VIA) for 1 h at 4° C. and then washed with 1% BSA-PBS. The cells were further stained with PE-conjugated anti-mouse IgG (Dako, Cat #R0480) for 30 minutes at 4° C., and washed again. Samples were analyzed on a BD LSRII flow cytometer (Becton Dickenson, San Jose, Calif.) and mean fluorescence intensity (MFI) reported.
Complement Dependent Cytotoxicity Assay.

We performed complement dependent cytotoxicity assays using our previously published protocol in Morse et al. 2010. Briefly, target cells were incubated with rabbit serum (1:100) as a source of complement and the HER3-VIA or GFP-VIA in sera from mice immunized as above diluted (1:100), or Trastuzumab (20 meg/ml) at 37° C. for 2 hrs. After incubation, cytotoxicity was measured using the Cyto-Tox 96 Nonradioactive Cytotoxicity Assay (Promega; per manufacturer's instructions) to measure LDH release in the culture media as evidence of cytotoxicity.

Assessment of HER3 Internalization

Human HER3+ breast cancer cells (SKBR3 and BT474M1) were incubated with 1:100 HER3-VIA or GFP-VIA at 37° C. for 60 minutes. After washing, fixation with 4% PFA, and permeabilization with permeabilizing solution 2 (Becton Dickenson), nonspecific binding was blocked with 2.5% Goat Serum at 37° C. for 30 min. Cells were incubated with 1:100 Red™-conjugated anti-mouse IgG (H+L) (Jackson ImmunoResearch Laboratories Inc. West Grove, Pa.) in a dark chamber for 1 hour at room temperature and washed with PBS. Slides were mounted in VectaShield containing DAPI (Vector Laboratories, Burlingame, Calif.) and images acquired using a Zeiss Axio Observer widefield fluorescence microscope (Carl Zeiss, Münchhen-Hallbergmoos, Germany).

Treatment of Established HER3+BT474M1 Human Tumor Xenografts by Passive Transfer of Vaccine Induced Antibodies.

Eight to 10 week old NOD.CB 17-Prkdc$^{scid}$/J mice (Jackson Labs., Bar Harbor, Me.) were implanted in the back with 17 Beta-Estradiol pellets (0.72 mg 60 day continuous release pellets; Innovative Research of American, Sarasota, Fla.) two days prior to tumor implantation. Five million BT474M1 tumor cells in 50% Matrigel were injected into the mammary fat pad. Tumors were allowed to develop for 14 days and then mice were randomized to receive iv injection of either GFP-VIA or HER3-VIA (5 mice per group). 100-150 microliters of VIA was injected at 2-3 day intervals for a total of 10 administrations. Tumor growth was measured in two dimensions using calipers and tumor volume determined using the formula volume=½ [(width)$^2$× (length)].

Treatment of Established HER3+Lapatinib-resistant rBT474 Human Tumor Xenografts by Passive Transfer of Vaccine Induced Antibodies.

Eight to 10 week old NOD.CB17-Prkdc$^{scid}$/J mice (Jackson Labs., Bar Harbor, Me.) were implanted in the mammary fat pad with 1 million lapatinib-resistant rBT474 tumor cells in 50% Matrigel. Tumors were allowed to develop for two months and then mice were randomized to receive iv injection of either GFP-VIA or HER2-VIA (5 mice per group). 100-150 microliters of VIA was injected at 2-3 day intervals for a total of 10 administrations. Tumor growth was measured as described above.

Statistical Analyses.

Tumor volume measurements for in vivo models were analyzed under a cubic root transformation to stabilize the variance as in Morse et al. 2010. Welch t-tests were used to assess differences between mice injected with HER3-VIA or control GFP-VIA. Analyses were performed using R version 2.10.1. For all tests, statistical significance was set at p<0.05.

Results

Ad-HER3 Elicits Anti-HER3 T Cell and Antibody Responses In Vivo

Figure 1C:
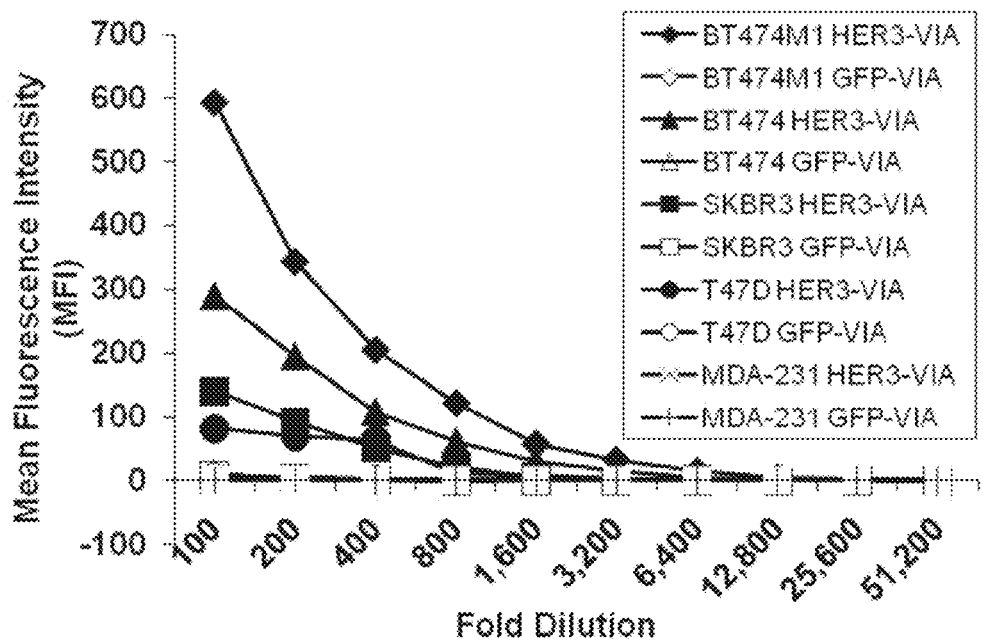
FIG. 1C is a graph showing the mean fluorescence intensity which was calculated for the binding of HER3-VIA against a panel of human breast cancer cell lines with dilutions of the serum.
Figure 1B:
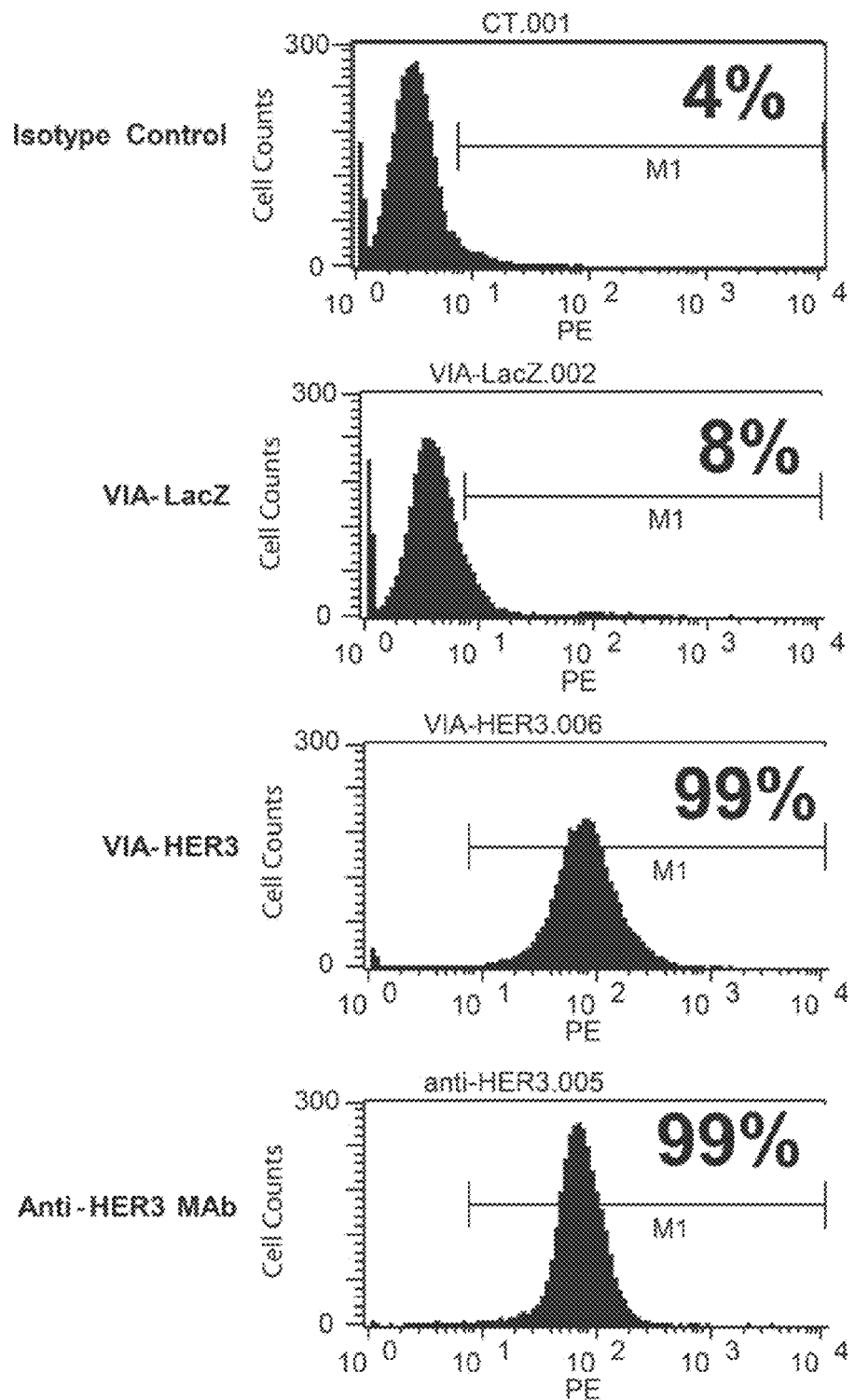
FIG. 1B is a set of FACS analysis histograms of peripheral blood serum from the mice was tested for the presence of antibodies capable of binding to tumor cell-expressed HER3. Flow cytometric analysis was used and histograms denote binding of HER3-vaccine induced antibodies (HER3-VIA) in serum to human breast cancer cell line BT474.

We developed a recombinant E1-, E3-adenovirus serotype 5 vector (Ad-HER3) expressing full length human HER3 (Ad-HER3). Wild type BALB/c mice were vaccinated with Ad-HER3, splenocytes from vaccinated mice were harvested and demonstrated by ELISPOT to specifically recognize HER3 using an overlapping human HER3 peptide mix as a source of antigens, whereas splenocytes from mice receiving control Ad-GFP vaccine or saline showed no reactivity to the HER3 peptide mix (FIG. 1A). To detect HER3-specific antibodies capable of detecting membrane associated HER3, binding of vaccine induced antibodies (VIA) in mouse serum was tested using a series of human HER3 expressing breast tumor cells lines, including the high HER3 expressing BT474M1, BT474, SKBR3 andT47D and the low to negatively expressing MDA-231 tumor cell line (FIGS. 1B and 1C). The serum of mice vaccinated with the Ad-HER3 had binding titers of >1:800, whereas the serum of mice receiving the control Ad-LacZ vaccine showed only background levels of binding. Thus, HER3-VIA are able to bind to endogenous HER3 expressed on human breast cancer lines.

To confirm that multiple HER3 epitopes were recognized, we demonstrated VIA binding to a series of HER3 peptides. The HER3-VIA recognized at least 18 epitopes in both the intracellular and extracellular domain, demonstrating that the antibody responses are polyclonal (FIG. 1D and SEQ ID NOs: 5-22). It should be noted that peptide arrays do not recapitulate conformationally correct protein structure, so they often underestimate the true number of epitopes recognized.

Figure 2A:
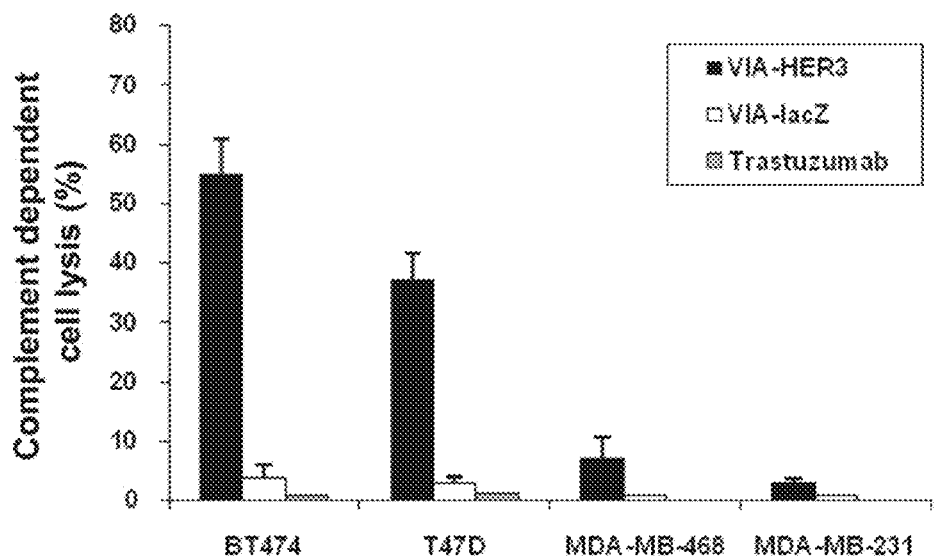
FIG. 2A is a set of graphs showing that HER-3 VIA mediate complement dependent cytotoxicity (CDC) against HER3-expressing (BT474, T47D, MDA-MB-468, BT474M1) human breast cancer cell lines but not against the HER3-negative cell line (MDA-MB-231). Black bars, HER3-VIA; white bars, GFP-VIA; grey bars, Trastuzumab. Trastuzumab does not mediate CDC.
Figure 2A:
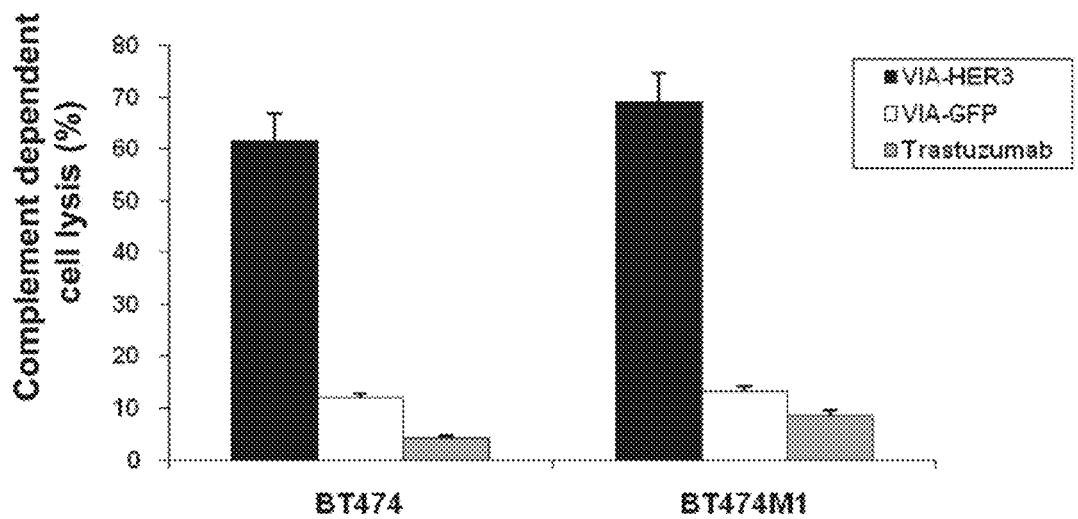

HER3 Specific Antibodies Induced by Vaccination (HER3-VIA) Mediate Complement Dependent Lysis of HER3+ Breast Tumor Cell Lines In Vitro Direct antibody-mediated tumor cell killing is a powerful potential mechanism of action of antibodies induced by vaccination. We evaluated the capacity HER3-VIA to mediate complement-dependent cytotoxicity (CDC). HER3-VIA exhibited strong CDC against HER3-expressing human breast tumor cells but not the HER3 negative MDA-231 cell line, while control GFP-VIA showed no effect (FIG. 2A). Trastuzumab is known not to mediate CDC and this was confirmed in our assays.

Anti-proliferative Effects of HER3 VIA In Vitro

Although immunization with Ad-HER3 was able to efficiently induce humoral immunity in vivo and mediate complement dependent tumor cell cytotoxicity, we also wished to determine whether these antibodies could inhibit tumor cell proliferation. We found that when HER3-expressing human breast cancer cells were cultured with HER3-VIA from the sera of Ad-HER3 vaccinated mice, their proliferation was significantly inhibited compared with cells cultured with control GFP-VIA (FIG. 2B). Of interest, despite the much high levels of HER2 expressed on these tumor cells, compared to HER3, the inhibition of tumor cell proliferation mediated by HER3-VIA was similar to the effects of the clinically effective monoclonal antibody trastuzumab.

Loss of HER3 Expression on Tumor Cell Lines Mediated by HER3-VIA In Vitro

Figure 2C:
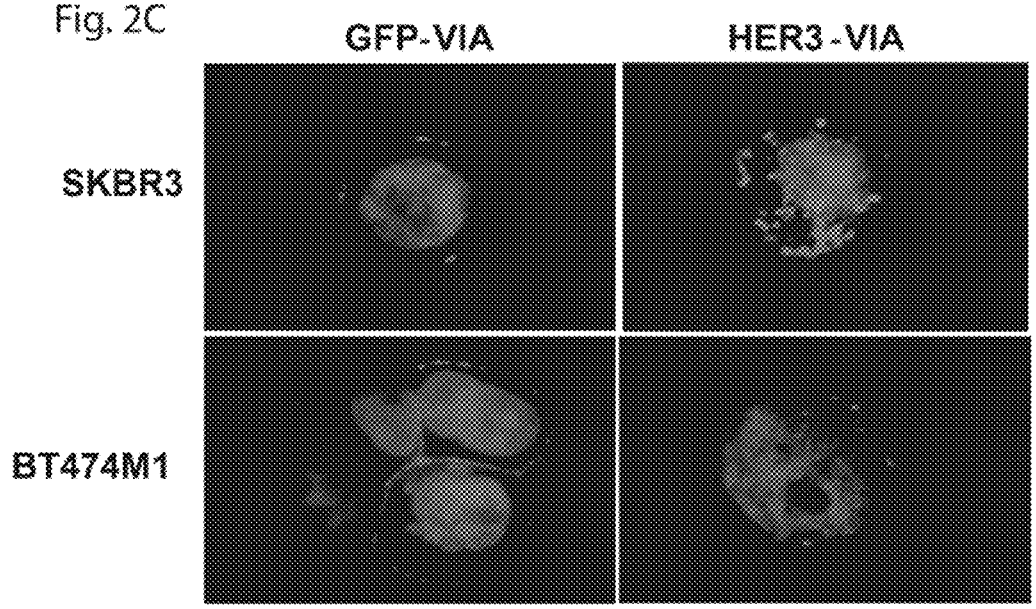
FIG. 2C is a set of photographs showing that binding of HER3-VIA results in rapid internalization of endogenous HER3 receptor expressed on the surface of human breast cancer cell lines.

Growth factor receptor internalization, degradation, and down regulation has been proposed as a mechanism for the inhibition of tumor growth mediated by monoclonal antibodies. To ascertain whether receptor down regulation was caused by HER3-VIA as a result of receptor internalization, we visualized cell membrane associated HER3 receptor on SKBR3 and BT474M1 tumor cells. When exposed to serum containing HER3-VIA or GFP-VIA, dramatic internalization and aggregation of the receptor was observed within 1 hr after exposure to HER3-VIA, but not with exposure to control GFP-VIA (FIG. 2C).

Figure 3A:
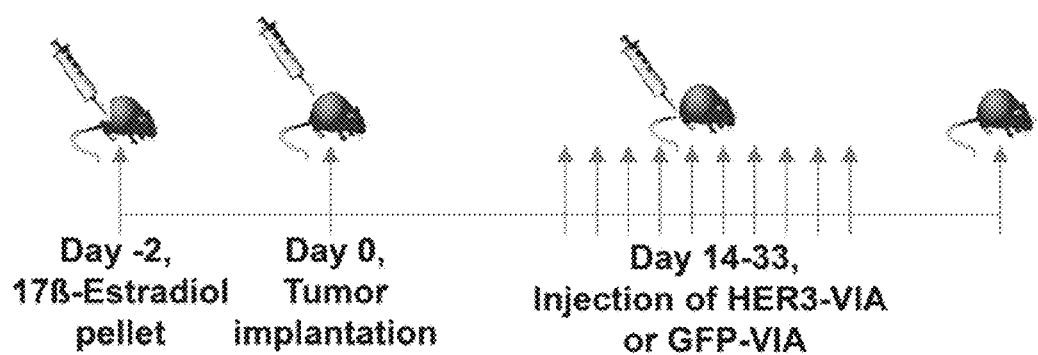
FIG. 3A is a cartoon showing the experiment schema. HER3-VIA or control GFP-VIA were transferred via tail vein injections.
Figure 3B:
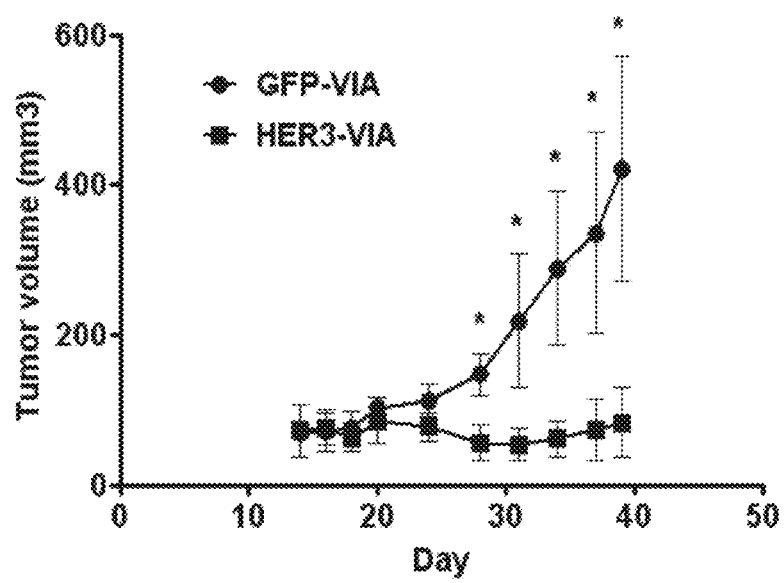
FIG. 3B is a graph showing that HER3-VIA retarded the growth of established BT474M1 breast cancers (p<0.005 at *)

Inhibition of Tumor Growth by HER3 VIA In Vivo is Associated with Loss of HER3 Expression and Anti-signaling Effects After finding that HER3 specific antibodies could inhibit HER3+ tumor cell proliferation in vitro, we sought to demonstrate the effects of HER3 VIA in vivo. At this time, there are no murine breast tumors dependent on human HER3 for growth, and attempts to establish 4T1 tumors expressing HER3 have been unsuccessful. Consequently, we employed a human xenograft model using the BT474M1 cell line that expresses both HER2 and HER3, with adoptive transfer of antibodies to demonstrate the in vivo activity of HER3-VIA. The study design is illustrated in FIG. 3A. We found that passive immunotherapy with HER3-VIA retarded the growth of established HER3+BT474M1 human tumor xenografts in vivo (p<0.005 after Day 28) when compared to the control GFP-VIA treated mice (FIG. 3B). At the termination of the study tumor size was compared and was significantly reduced in the HER3-VIA-treated mice (p=0.005).

Figure 3C:
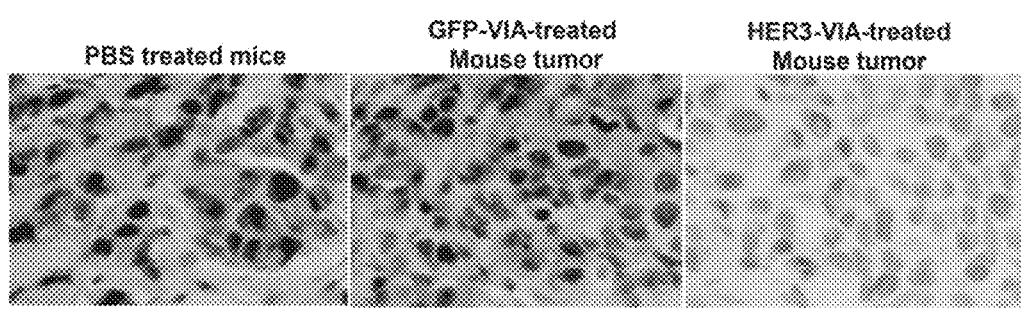
FIG. 3C is a set of photographs showing immunohistochemistry analysis of HER3 protein expression in excised tumors and revealed a dramatic loss of HER3 protein in the HER3-VIA-treated mice compared to GFP-VIA treated mice. GFP-VIA-treated mouse tumors retained HER3 protein levels seen in tumors from mice "treated" with saline.

In addition to demonstrating anti-tumor effects in vivo, we also wanted to document the anti-HER3 signaling effects of HER3 VIA in vivo. Analysis of excised tumors allowed us to determine HER3 expression following treatment in vivo. We found that mice treated with HER3-VIA showed decreased levels of HER3 in their residual tumor by immunohistochemistry (FIG. 3C), consistent with antigen downregulation as the basis of immunologic escape. We also examined the impact of treatment with HER3-VIA on downstream effectors of HER3 signaling, and found a reduction of pHER (pTyr), HER3, and pErkl/2, compared to tumors treated with GFP-VIA (FIG. 3D).

Inhibition of Therapy-resistant Tumor Growth by HER3 VIA In Vivo

Figure 4A:
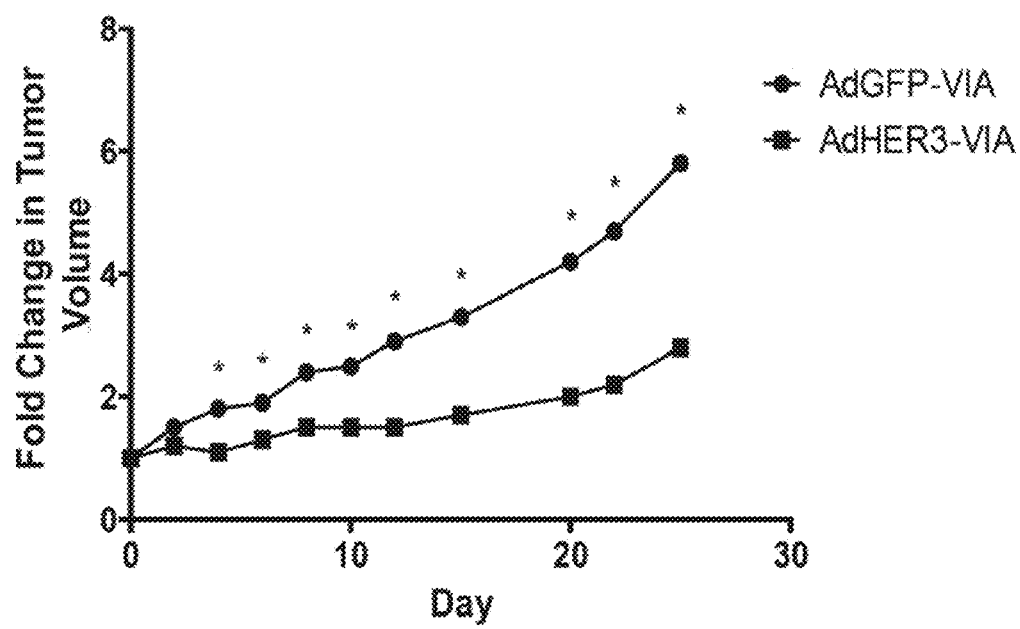
FIG. 4A is a graph showing that passive transfer of HER3-VIA retarded the growth of established lapatinib-refractory BT474 tumors in SCID mice demonstrating that anti-HER3 immunity can treat therapy resistant tumors (p<0.025 at *).
Figure 4C:
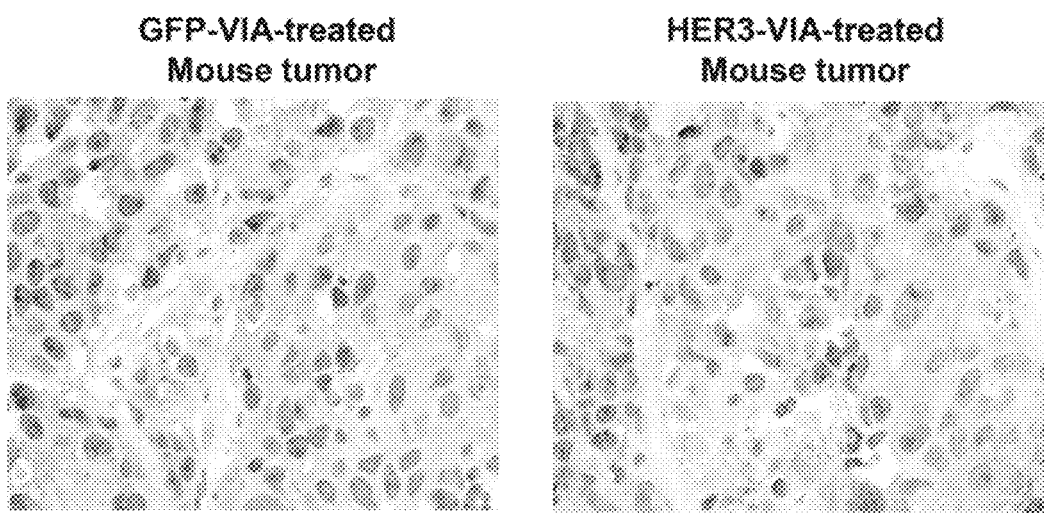
FIG. 4C is a set of photographs showing immunohistochemical analysis of excised tumors and revealed no significant change in HER3 levels compared to controls.

While the antitumor efficacy against established HER3+ BT474M1 tumors was encouraging, we know that a major unmet need for breast cancer patients is for therapies to overcome therapeutic resistance to HER2 targeted therapies. For example, therapeutic resistance to trastuzumab, can be overcome by treatment with a small molecule inhibitor of HER2, lapatinib, but patients whose tumors initially respond ultimately experience therapeutic resistance and disease progression. Of interest is the persistent overexpression of HER2 in the tumors from these patients, and the emerging recognition that signaling from the HER2/HER3 heterodimer, and other heterodimers involving HER3, was a significant resistance mechanism. Consequently, we tested the effects of HER3-VIA in a model of lapatinib resistance derived from the rBT474 cell line that we have previously reported. Xia et al. A model of acquired autoresistance to a potent ErbB2 tyrosine kinase inhibitor and a therapeutic strategy to prevent its onset in breast cancer. Proc Natl Acad Sci USA 2006; 103:7795-800. This rBT474 cell line expresses HER2 and HER3 at similar levels to the BT474M1 tumor line. We demonstrate that the HER3-VIA was effective at retarding the growth of established tumors (FIG. 4) (p 0.025 for all time points from Day 4 to Day 25), confirming the therapeutic potential of an Ad-HER3 vaccine for patients who have experienced disease progression on lapatinib.

Figure 4B:
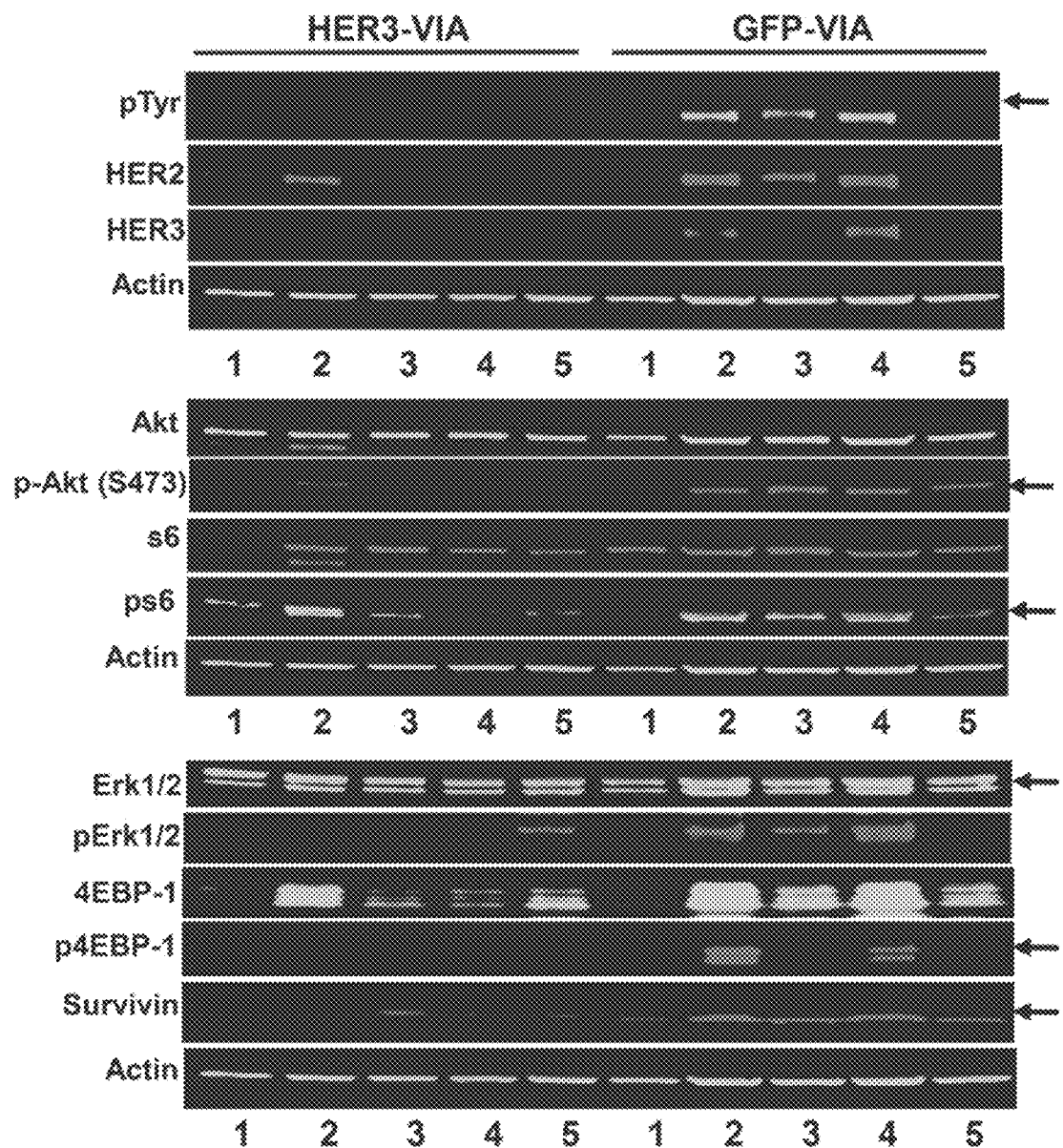
FIG. 4B is a set of photographs showing Western blot analysis of excised tumors to perform pathway analysis.

Inhibition of Lapatinib-resistant Tumor Growth by HER3 VIA In Vivo is Associated with Loss of HER3 Expression and Broader Anti-signaling Effects than Lapatinib-sensitive Tumors Tumors excised from the mice at the termination of the study described above, were examined for signaling pathway modulation. Whole tumor lysates from 5 mice per group were studied, since we expected some mouse-to-mouse variation and wanted to capture the spectrum of responses (FIG. 4B). Total HER2 and HER3 levels are decreased in the HER3-VIA treated tumors, suggesting receptor degradation may be occurring. pTyr is also consequently reduced, indicating decreased HER2:HER3 signaling. pAkt473(S473) and pS6 are also decreased for the HER3-VIA treated tumors, as are pErk 1/2, p4EBP1, and survivin relative to the control GFP-VIA treated tumors. In contrast to the data in the lapatinib-sensitive BT474M1 tumors, immunohistochemistry analysis of excised rBT474 tumors did not show a marked decrease in HER3 in tumors treated with HER3-VIA compared to GFP-VIA controls (FIG. 4C), suggesting that HER3 degradation was more modest and anti-proliferative effects mediated through the HER3 heterodimers were therefore more prominent.

Generate Ad5(E2b-)HER3 and Ad5(E2b-)HER3 C1C2 constructs (Y1, Q1-2)

Adenoviral vectors expressing HlER3 using the Ad5 (E2b-) platform have been constructed and have been used to generate virus. We now wanted to assess whether other HER3 expressing adenovirus vectors would have similar effects. We have modified the adenovirus construction methods to facilitate the construction of (E1-, E2b-, E3-) Ad5 vector.

Figure 5:
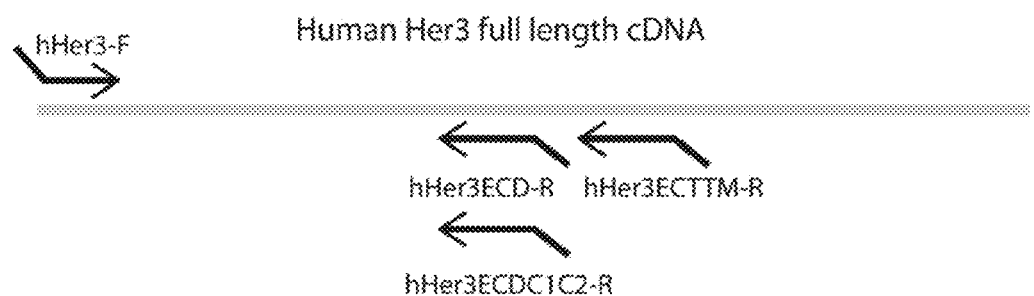
FIG. 5 is a schematic representation of the primer binding sites on the human Her3 full length cDNA.

The human HER3 full length cDNA was obtained from OriGene (Rockville, Md.). The truncated HER3 extracellular domain (ECD) and HER3 ECD plus transmembrane (TM) sequence were created using HER3 full length as templates in a PCR reaction using primers (see Table I below) and FIG. 5.

TABLE 1

Primers used in construction of truncated Ad5-human HER3

| Primer | Sequence (SEQ ID NO:) |
|---|---|
| hHER3-F | 5'-cagggcggccgcaccatgagggcgaac gacgctct-3' (SEQ ID NO: 23) |
| hHER3-ECDTM-R | 5'-acaagcggccgcagttaaaaagtgccg cccagcatca-3' (SEQ ID NO: 24) |
| hHER3-ECD-R | 5'-acaagcggccgcatttatgtcagatgg gttttgccgatc-3' (SEQ ID NO: 25) |
| hHER3-ECDC1C2-R | 5'-acaagcggccgcattgtcagatgggtt ttgccg-3' (SEQ ID NO: 26) |

Briefly, full length HER3 cDNA and the PCR product are cut by restrict enzyme Not I and subcloned into Not I digested pShuttle-CMV or pShuttleCMV-C1C2 plasmid. Confirmation of correct insert of the full length and truncated DNA within pShuttle-CMV or pShuttle-CMV-C1 C2 was confirmed by DNA sequencing. The pShuttle-CMV-her3-FL (full-length), pShuttle-Her3ECD, pShuttle-Her3ECDTM and pShuttle-Her3ECDC1C2 were then linearized using digestion with Pme I, recombined into linearized (E1-, E2b-, E3-) serotype 5 pAd construct in BJ 5183 bacterial recombination-based system (Stratagene), and propagated in XLI 0-Gold Ultracompetent cells (Stratagene). Complementing C7 cell (which express E1 and E2b) were used to produce high titers of these replication-deficient Ad5 vectors, and cesium chloride density gradient was done to purify the Ad5-vectors. All Ad vectors stocks were evaluated for replication-competent adenovirus via PCR-based replication-competent adenovirus assay.

The next generation human HER3 (E1-, E2b-, E3-) Adenovirus vectors are as follows:
1. Ad5 (E2b-)HER3 FL; express human HER3 full length.
2. Ad5 (E2b-)HER3 ECDTM; express human HER3 ECD and trans-membrane domain
3. Ad5 (E2b-)HER3 ECD; express human HER3 ECD
4. Ad5 (E2b-)HER3 ECDC1C2; express human HER3 ECD and C1C2 domain The ability of each vector to induce a HER3 specific immune responses will be tested, but was expected based on the earlier results and epitopes identified above. Human HER3 specific immune responses to the vectors will be measured in Balb/c mice and in human HER3 transgenic mice.

Figure 6:
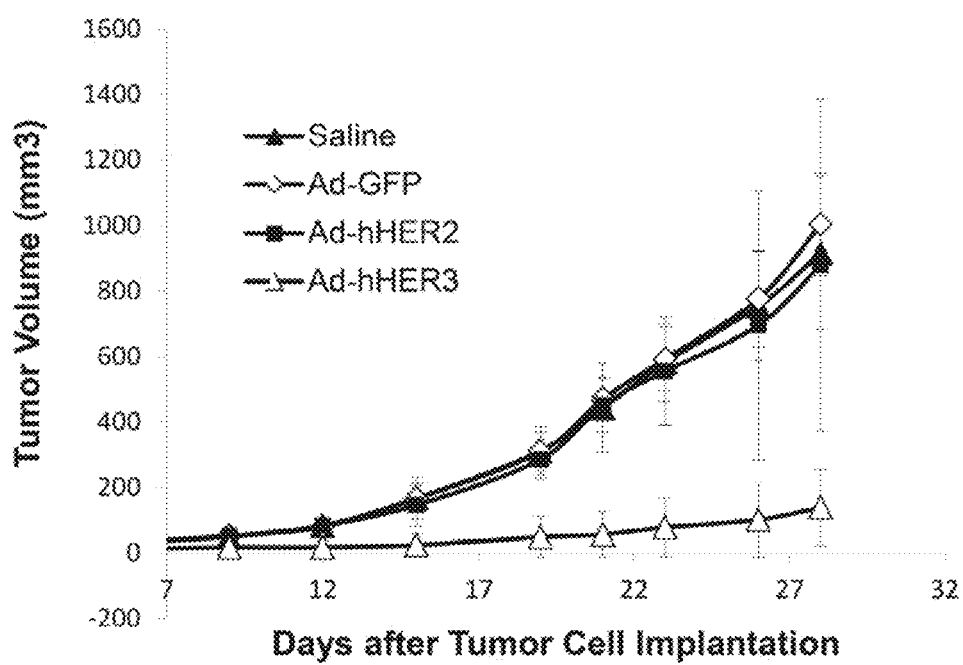
FIG. 6 is a graph showing that Ad-HER3 vaccine inhibits JC-HER3 tumor growth. Balb/c mice were vaccinated twice (day-18, day-4) via footpad injection with Ad-GFP or Ad-hHER3 vectors ($2.6 \times 10^{10}$ particles/mouse). Four days after boosting, at day 0, each mouse was implanted with 1,000,000 JC-HER3 mouse mammary tumor cells expressing human HER3. Tumor volume was measured, once it became palpable, every 3 days using calipers and is reported.
Figure 7:
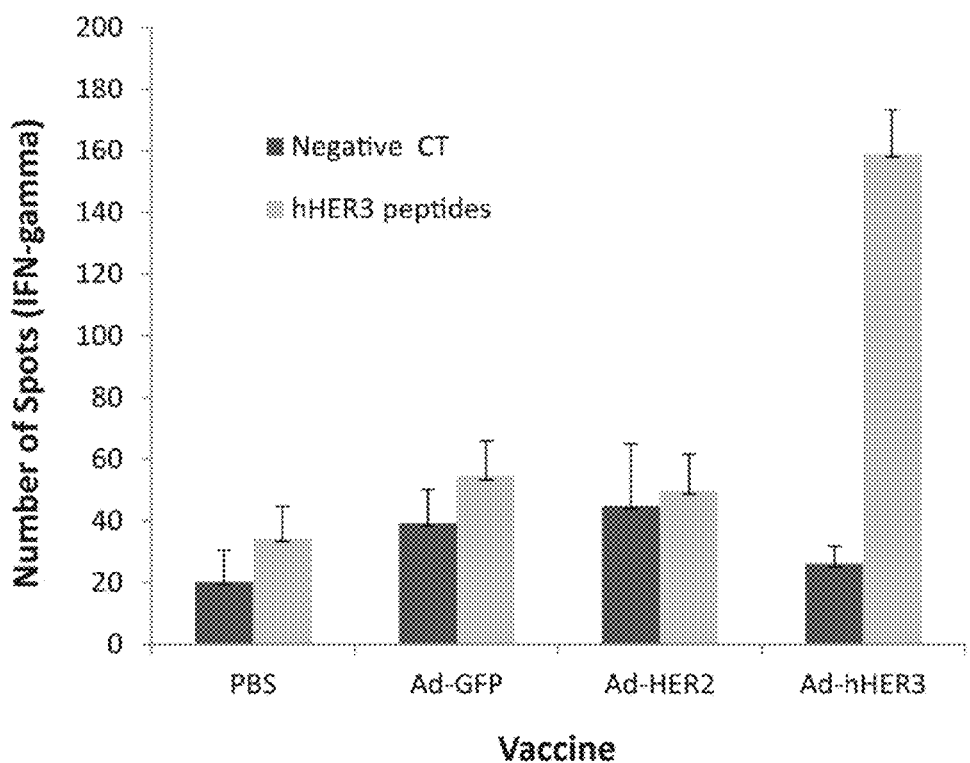
FIG. 7 is a graph showing Ad-hHER3 vaccine induced HER3 specific T cell response. Splenocytes (500,000 cells/well) from vaccinated Balb/c mice in FIG. 6 (x-axis) were collected at day 28 and stimulated with HER3 peptide mix (hHER3 peptides) (1 g/mL was used; JPT, Acton, Mass.) or HIV peptide mix (BD Bioscience) as a negative control (Negative CT) and analyzed in a interferon-gamma ELISpot assay.

To determine the preventive effect of HER3 vacccination, we have established a HER3 prevention model using JC-HER3 mouse mammary tumor cells in Balb/c mice. As shown in FIG. 6, only vaccination with the HER3 encoding vector prevented growth of the hHER3 expressing tumors in vivo. We next sought to demonstrate development of HER3 specific immune response by ELISPOT. Results are shown in FIG. 7.

Figure 8:
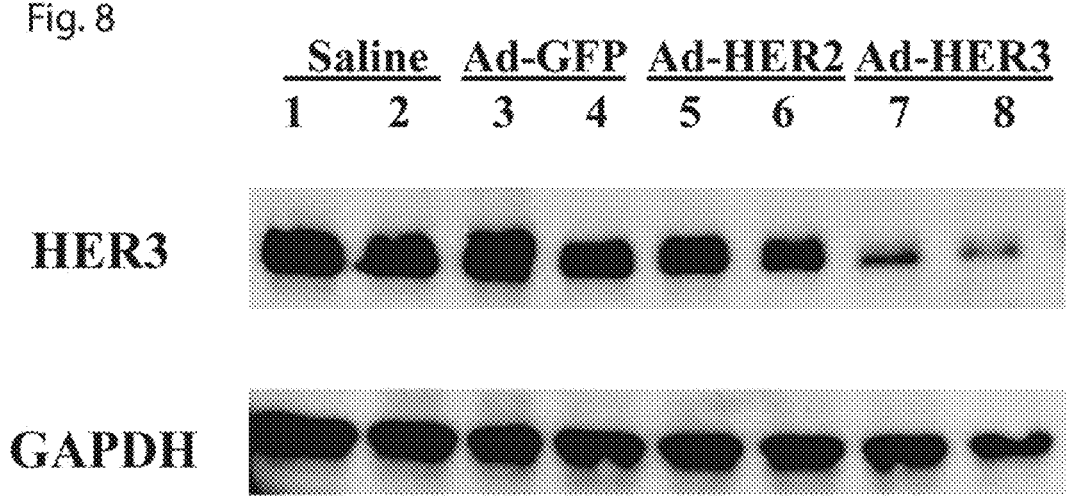
FIG. 8 is a set of photographs showing that Ad-hHER3 vaccination causes degradation of HER3 on JC-hHER3 tumor. Tumors were isolated from vaccinated and control Balb/c mice (as indicated on figure) and immediately flash frozen. Tissue extracts were prepared by homogenization in RIPA buffer. Equal amounts of protein from each sample were used to visualize the indicated molecules by immunoblotting.

Due to the induction of HER3 specific immune responses, we sought evidence whether those tumors that did grow in the HER3 vaccinated mice expressed HER3. In other words, we sought evidence of loss of HER3 in those tumors capable of growth in the vaccinated mice. As shown in FIG. 8, immunization with Ad-hHER3 led to a reduction of HER3 expression in the tumors that did develop. Of interest, immunization with Ad-GFP or Ad-hHER2 did not change HER3 expression.

Figure 9:
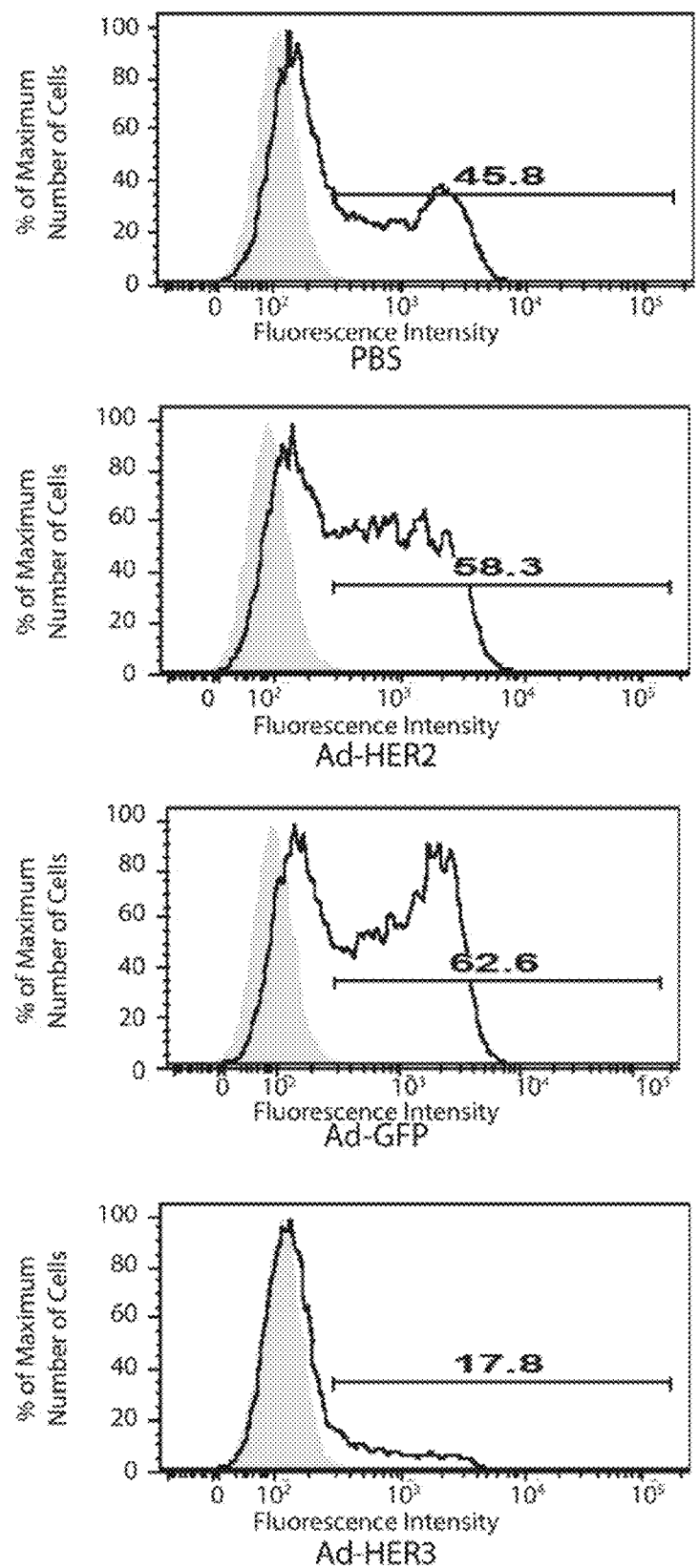
FIG. 9 is a set of FACS histograms showing that Ad-hHER3 vaccination decreases HER3 expression on JC-hHER3 tumor cells. JC-HER3 tumors were collected from vaccinated and control Balb/c mice (as indicated on figure) at day 28 and pooled by group. The tissues were minced and digested with an enzymatic cocktail (Hyaluronalse, DNAse, and Collagenase) overnight. After 3 days culture, the cells were harvested and HER3 expression determined by flow cytometry using PE-anti-hHER3 antibody.

We then tested for surface HER3 expression in the tumors that grew in the HER3 vaccinated mice. As demonstrated in FIG. 9, the surface expression of HER3 was dramatically reduced in the tumors that did grow in the HER3 vaccinated mice.

In summary, we created a HER3 vaccine by generating a recombinant adenovirus encoding human HER3 (Ad-HER3). The Ad-HER3 was highly effective in eliciting significant HER3 specific T-cell and polyclonal antibody responses in mouse models, with the vaccine induced antibodies (VIA) binding multiple HER3 epitopes as well as tumor-expressed HER3 and mediating complement dependent lysis. In addition, the HER3-VIA caused HER3 internalization and degradation, significantly inhibited signaling mediated by receptor heterdimers involving HER3, and retarded tumor growth in vitro and in vivo. Critically, we also showed that the HER3-VIA retarded the growth of human breast cancer refractory to HER2 small molecule inhibitors (lapatinib) in SCID xenografts, providing a compelling argument for the Ad-HER3 vaccine to be tested in patients whose cancer has progressed on HER2 targeted therapy, and in combination with HER2 targeted therapy.

It is interesting to note that the lapatinib-resistant rBT474 clone is much more sensitive to HER3-VIA in vivo than the lapatinib-sensitive BT474M1 clone yet they express equivalent levels of HER3 on the cell surface, which may be a result of increased reliance on HER3 as a driver of tumor growth in the lapatinib resistant BT474 cells. In fact, treatment of the lapatinib resistant BT474 cells leads to decreased HER3, pHER3 and pERKI/2 as expected, but also decreased HIER2, pAkt(S473), pS6, p4EPB1, and survivin expression. In contrast, treatment of the lapatinib sensitive BT474 cells with HER3 VIA decreases only HER3, pHER3 and pErk 1/2, suggesting that HER3 VIA will have more profound biologic and clinical effects in lapatinib refractory tumors. The lapatinib-resistant BT474 cells also continue to express HER3 protein after treatment with HER3-VIA in vivo, suggesting that antigen loss is not an escape mechanism for lapatinib resistant tumors because HER3 is critical to the tumor survival. Thus, persistent expression of HER3 because of it' role in lapatinib resistance, ensures that tumors will remain targets for vaccine induced T cell and antibody response.

The decrease in the inhibitor of apoptosis protein survivin suggests that a mechanism of resistance to tumor cell killing is also being diminished. We observed similar effects on the expression of survivin in the mouse 4T1-HER2 tumor model which is relatively resistant to trastuzumab, but relatively sensitive to lapatinib. When the 4T1-IHER2 expressing tumors were treated with lapatinib or HER2 VIA alone, we observed no change in survivin expression, but when these tumors were treated with a combination of lapatinib and HER2-VIA we observed a decrease in survivin expression, implying that complete HER2 signaling blockade decreased survivin expression. In an analogous fashion, it suggested that complete blockade of HER2:HER3 signaling in lapatinib refractory tumors is accomplished by treatment with HER3-VIA, resulting in the decreased expression of survivin in these studies.

We believe our findings have relevance for counteracting the development of resistance to HER2 targeted therapies. Although HER3 is non-transforming alone, recent data suggests that HER3 expression or signaling is associated with drug resistance to targeted therapies directed against other HER family members. In particular, the acquired resistance to HER2 inhibitors in HER2-amplified breast cancers, trastuzumab resistance in breast cancer, with EGFR inhibitors in lung cancers, with pertuzumab resistance in ovarian cancers, and with EGFR inhibitors in head and neck cancers. The overexpression of HER2:HER3 heterodimers is also negatively correlated with survival in breast cancer. Our approach of targeting HER3 may also have advantages over other HER family targeting strategies. For example, data suggest that trastuzumab is effective against HER1:HER2 heterodimers but not HER2:HER3 heterodimers. HER3 may play a role in therapeutic resistance to other therapies including anti-estrogen therapies in ER positive breast cancers, with hormone resistance in prostate cancers, and with IGF1R inhibitors in hepatomas. Therefore, targeting HER3 may have relevance for counteracting resistance to other pathway inhibitors.

These data suggest that it may be possible to begin a "resistance prophylaxis" vaccination against overexpressed or mutated proteins that will predictably arise to mediate therapeutic resistance, such as HER3. Immunization against these proteins prior to their overexpression as a mediator of therapeutic resistance may avoid immune tolerance induced by their prolonged expression in an immunosuppressive microenvironment. The resulting pre-existing immune response would be much more effective in mediating anti-tumor responses to tumors overexpressing antigen, and/or prevent these mediators from being expressed.

We claim:

1. A composition comprising a DNA vaccine vector or an adenovirus or adeno-associated virus vaccine vector comprising a polynucleotide encoding a HER3 polypeptide fragment consisting of at least one of SEQ ID NOs: 5-8, 10-22, and a fragment of SEQ ID NO: 2 consisting of amino acids 1-663, wherein the vaccine vector expresses the HER3 polypeptide fragment.

2. The composition of claim 1, wherein the vaccine vector is selected from adenovirus or adeno-associated virus (AAV).

3. A method of treating a cancer or precancer or of reducing the likelihood of the cancer developing resistance to a cancer therapeutic comprising administering the composition of claim 1 to a subject having the cancer or precancer, wherein administration of the composition to the subject treats the cancer or precancer, reduces the likelihood of the cancer or precancer developing resistance to the cancer therapeutic or reverses resistance of the cancer or precancer to the cancer therapeutic.

4. The method of claim 3, wherein the composition is administered concurrently with, before or after administration of the cancer therapeutic.

5. The method of claim 4, wherein the cancer therapeutic is an agent targeting HER2, HER1, estrogen receptor, EGFR, or IGF1R or is selected from the group consisting of trastuzumab, lapatinib, cetuximab, pertuzumab and erlotinib.

6. The method of claim 3, wherein the cancer or precancer is selected from the group consisting of a breast, prostate, lung, ovarian, colon, rectal, pancreas, bladder, head and neck, liver and HER2 positive cancer or precancer.

7. The method of claim 3, wherein the subject develops an immune response to HER3.

8. The method of claim 7, wherein the immune response includes at least one of antibody-dependent cellular cytotoxicity, polyclonal antibody response, complement dependent cellular cytotoxicity, cellular cytotoxicity, disruption of ligand binding, disruption of dimerization, mimicking ligand binding causing internalization of HER3, an antibody response, a T cell mediated response or degradation of HER3.

9. The method of claim 7, wherein the immune response comprises an antibody response directed to at least one of SEQ ID NOs: 5-8, 10-22.

10. The method of claim 3, wherein administration of the composition results in a reduction of HER3 expression on cancer or precancer cells after administration of the composition as compared to the level of HER3 on the cells prior to vaccination.

11. The method of claim 3, wherein administration results in decreased tumor growth rate or decreased tumor size after administration as compared to prior to administration.

12. A method of reducing the likelihood of a cancer or precancer developing resistance to a cancer therapeutic comprising administering the cancer therapeutic and the composition of claim 1 to a subject having a cancer or precancer.

13. The method of claim 12, wherein administration reduces the growth of the cancer or precancer.

14. The method of claim 12, wherein the cancer does not develop resistance to the cancer therapeutic.

15. The method of claim 12, wherein cancer or precancer that is resistant to the cancer therapeutic becomes more sensitive to the cancer therapeutic after administration of the composition.

16. The method of claim 12, wherein the composition is administered concurrently with, before or after administration of the cancer therapeutic.

* * * * *